(12) United States Patent
Umezu et al.

(10) Patent No.: US 8,193,008 B2
(45) Date of Patent: Jun. 5, 2012

(54) METHOD OF FORMING SEMICONDUCTOR THIN FILM AND SEMICONDUCTOR THIN FILM INSPECTION APPARATUS

(75) Inventors: Nobuhiko Umezu, Kanagawa (JP); Koichi Tsukihara, Kanagawa (JP); Hirohisa Amago, Kanagawa (JP); Go Matsunobu, Kanagawa (JP); Katsuya Shirai, Kanagawa (JP)

(73) Assignee: Sony Corporation, Tokyo (JP)

( * ) Notice: Subject to any disclaimer, the term of this patent is extended or adjusted under 35 U.S.C. 154(b) by 451 days.

(21) Appl. No.: 12/468,969

(22) Filed: May 20, 2009

(65) Prior Publication Data

US 2009/0291511 A1 Nov. 26, 2009

(30) Foreign Application Priority Data

May 23, 2008 (JP) ................................. 2008-135806
Jan. 30, 2009 (JP) ................................. 2009-020686

(51) Int. Cl.
*H01L 21/66* (2006.01)
(52) U.S. Cl. .................... 438/16; 438/487; 257/E21.53; 257/E21.09; 257/75; 257/70; 257/74
(58) Field of Classification Search .................... 438/16, 438/487; 257/E21.53, E21.09, 75, 70, 74; 356/433
See application file for complete search history.

(56) References Cited

U.S. PATENT DOCUMENTS 6,673,639 B2  1/2004  Wada et al.
6,977,775 B2  12/2005  Sasaki et al.

FOREIGN PATENT DOCUMENTS

JP  2002-319606  10/2002
JP  2003-332235  11/2003
JP  2004-153150  5/2004
JP  2005-101202  4/2005

*Primary Examiner* — Bradley K Smith
*Assistant Examiner* — Amar Movva
(74) *Attorney, Agent, or Firm* — SNR Denton US LLP

(57) ABSTRACT

A method of forming a semiconductor thin film includes the steps of: forming an amorphous semiconductor thin film on a substrate; forming a crystalline semiconductor thin film partially in each element region by applying laser light to the amorphous semiconductor thin film to selectively perform a heating process on the amorphous semiconductor thin film, thereby crystallizing the amorphous semiconductor thin film in a region irradiated with the laser light; and inspecting the crystallinity degree of the crystalline semiconductor thin film. The step of inspecting includes the steps of determining a contrast between the luminance of a crystallized region and the luminance of a non-crystallized region by applying light to the crystalline semiconductor thin film and the amorphous semiconductor thin film, and performing screening of the crystalline semiconductor thin film on the basis of the determined contrast.

20 Claims, 16 Drawing Sheets

|  | TRANSMISSION | ELLIPSOMETRY | Raman | SEM | TEM |
|---|---|---|---|---|---|
| NO DESTRUCTION | ○ | ○ | × | × | × |
| NO PREPROCESSING | ○ | ○ | × | × | × |
| TIME TO EVALUATION | ○ (~10 MIN) | ○ (~10 MIN) | × (~A FEW HOURS) | × (~A FEW DAYS) | × (1 WEEK OR MORE) |
| NUMERICAL QUANTIFICATION | ○ | × | ○ | × | × |
| MICROSCOPIC AREA | ○ | × | ○ | ○ | ○ |
| EVALUATION | ○ | × | × | × | × |
FIG. 11
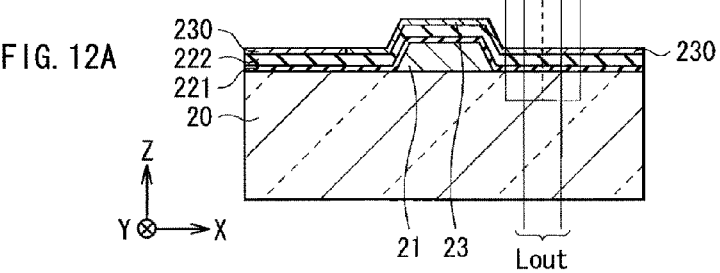
FIG. 12A
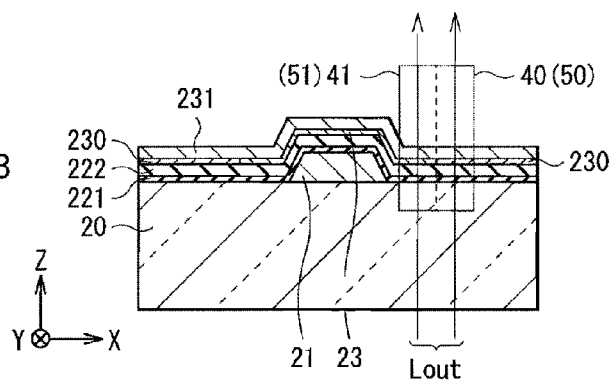
FIG. 12B

① OBTAINMENT OF MEASUREMENT IMAGE (D31)

② OBTAINMENT OF REFERENCE IMAGE (D32)

③ OBTAINMENT OF REFERENCE IMAGE (D33)

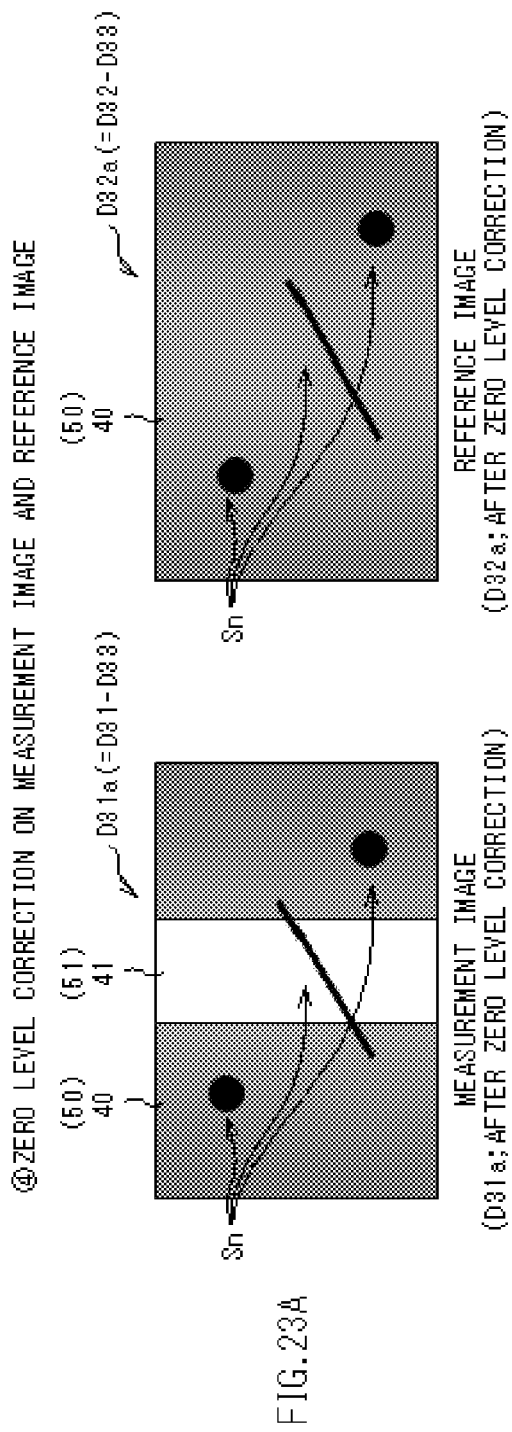
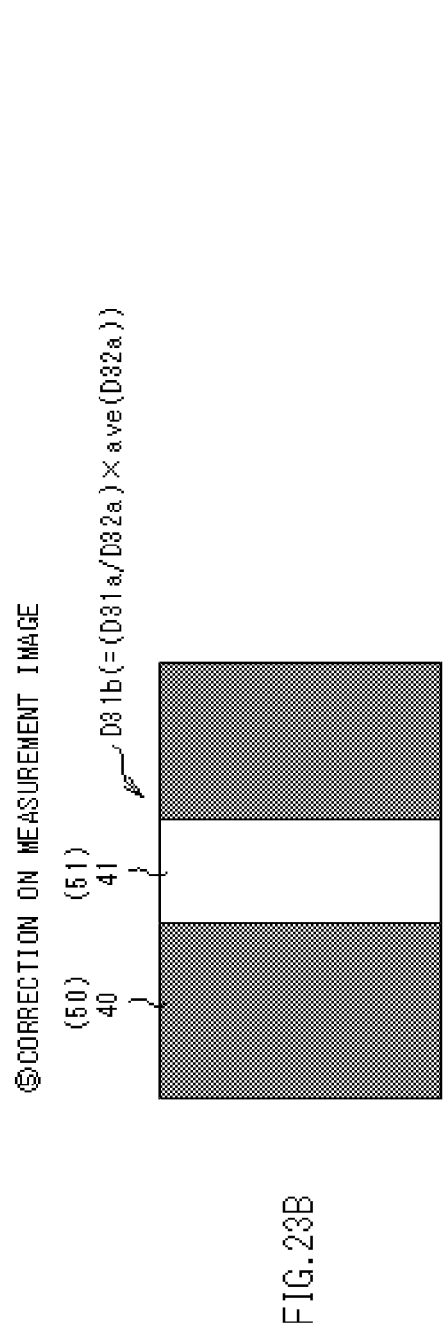
FIG. 23A
FIG. 23B

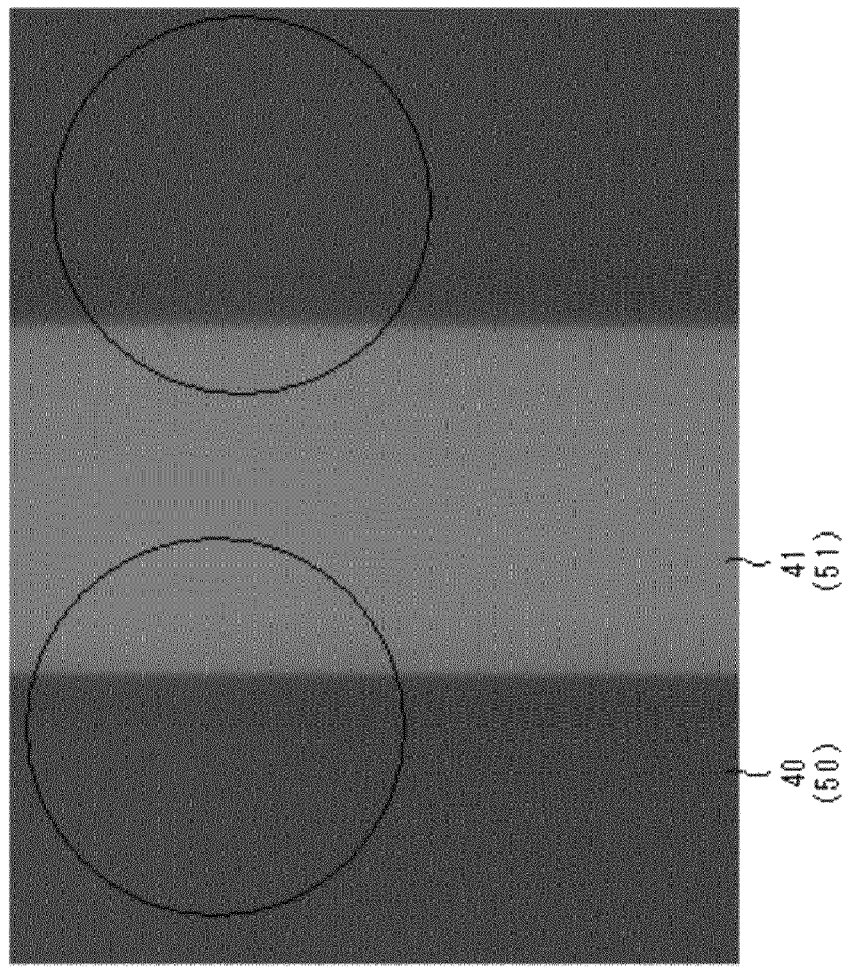

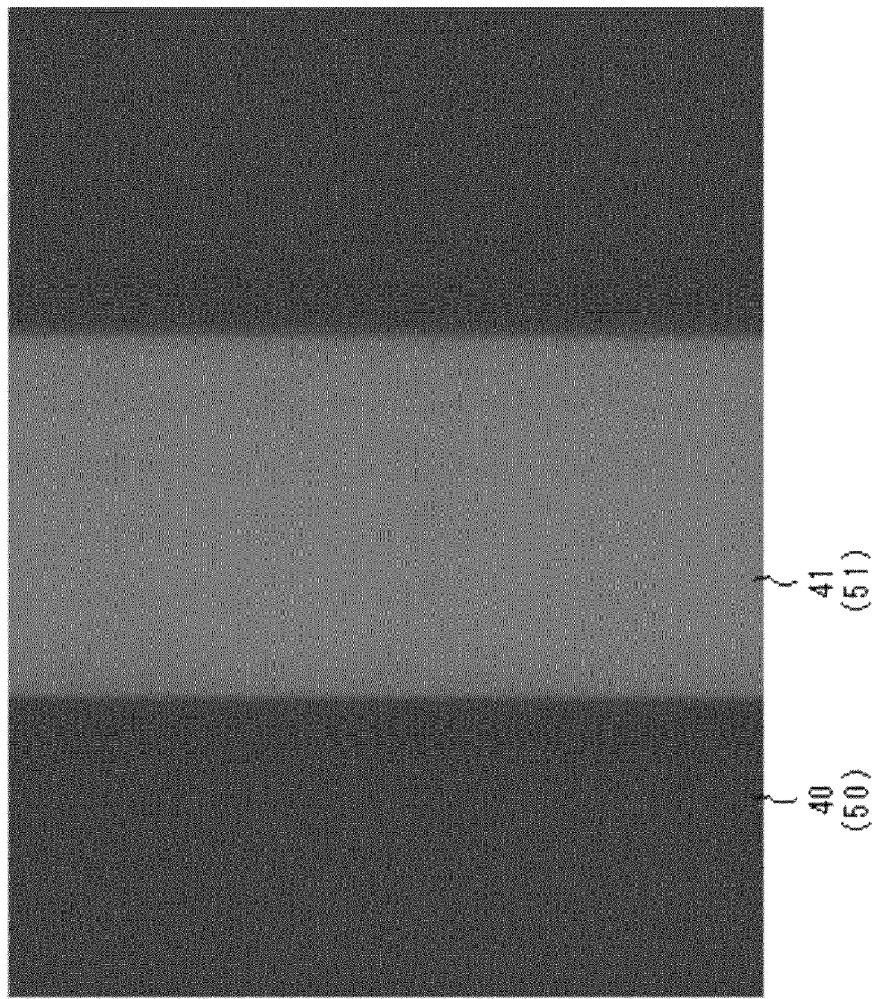

| | BEFORE CORRECTION (6σ) | AFTER CORRECTION (6σ) |
|---|---|---|
| VARIATIONS IN CONTRAST | 0.529% | 0.278% |

METHOD OF FORMING SEMICONDUCTOR THIN FILM AND SEMICONDUCTOR THIN FILM INSPECTION APPARATUS

BACKGROUND OF THE INVENTION

1. Field of the Invention

The present invention relates to a method of forming a semiconductor thin film suitable for manufacturing a TFT (Thin Film Transistor) substrate used in, for example, a liquid crystal display or an organic EL (ElectroLuminescence) display, and an inspection apparatus for such a semiconductor thin film.

2. Description of the Related Art

In an active matrix liquid crystal display or an organic EL display using an organic EL device, a TFT substrate is used. The TFT substrate is formed by forming a an amorphous semiconductor thin film or a polycrystalline semiconductor thin film with a relatively small particle diameter on a substrate, and forming a TFT as a drive element through the use of a semiconductor thin film crystal grown by annealing the amorphous semiconductor thin film or the polycrystalline semiconductor thin film by irradiation with a laser beam.

As a light source of an annealing apparatus using a laser beam, an excimer laser having high absorptance into the semiconductor thin film and obtaining a large pulsed light output has been hitherto used. However, since the excimer laser is a gas laser, pulses vary in output intensity. Therefore, TFTs formed through the use of the excimer laser vary in characteristics, thereby to easily cause display unevenness in a display using the TFTs.

Therefore, to prevent a decline in image quality due to variations in pulse intensity in the gas laser, an annealing apparatus using a laser diode with high output stability as a light source has been proposed as described in, for example, Japanese Unexamined Patent Application Publication No. 2003-332235. However, a light output obtained from the laser diode is very small, compared to that from the excimer laser or the like, so the size of a beam in an annealing process is also small. Therefore, an annealing process time per unit area of the TFT substrate is increased, thereby to cause a decline in productivity or an increase in manufacturing cost.

Thus, for the purpose of achieving a higher throughput in the annealing process, there is proposed an annealing method in which a plurality of laser light sources are arranged in proximity to one another and a plurality of laser beams from the plurality of laser light sources are simultaneously applied to a plurality of regions on an amorphous semiconductor thin film, thereby to reduce a scanning time and improve productivity as described in, for example, Japanese Unexamined Patent Application Publication No. 2004-153150.

On the other hand, a method of controlling crystallization of a semiconductor thin film through the use of such a laser diode has been performed by a laser beam intensity monitoring means included in an annealing apparatus. For example, in a method of monitoring laser beam intensity described in, for example, Japanese Unexamined Patent Application Publication No. 2005-101202, a single intensity measurement section is used for optical paths of a plurality of laser optical systems, so one intensity measurement section is moved over the optical paths of the laser optical systems so as to sense light on each of the optical paths, thereby the irradiation energy of each of the plurality of laser optical systems is measurable by one intensity measurement section.

Moreover, for example, Japanese Unexamined Patent Application Publication No. 2002-319606 discloses a method of evaluating the degree of crystallization in an annealed region (crystallized region) by determining a high level and a low level of luminance based on irradiation light in the annealed region. More specifically, the degree of crystallization is evaluated on the basis of a state of high crystallinity and low crystallinity in the crystallized region.

SUMMARY OF THE INVENTION

However, in the case where an annealing process is performed through the use of a plurality of laser beams as in the case of Japanese Unexamined Patent Application Publication No. 2004-153150, there is an individual difference in the divergence angle of emitted light among laser light sources. Moreover, even in the case where a uniform irradiation optical system is arranged to correct such an individual difference, an adjustment error or the like occurs. Therefore, in the case where the annealing process is performed through the use of a plurality of laser beams, a difference in the size or intensity of laser light applied to an object to be irradiated arises inevitably.

Moreover, in the case of Japanese Unexamined Patent Application Publication No. 2005-101202, only the intensity (power) of a laser beam from each of laser light sources is monitored, so it is difficult to monitor a fine difference in power density on a plane of an object to be irradiated due to a focus position, aberration of an optical system or the like. Therefore, such a difference in power density causes a difference in an annealing effect on the object (a semiconductor thin film), and a difference in crystallinity degree by a position on the semiconductor thin film, thereby as a result, depending on laser beams, formed TFTs vary in characteristics. Such a difference in characteristics among the TFTs may cause display unevenness in a display. Such a difference in a laser annealing effect on the semiconductor thin film (a difference in an effect by a position on a thin film) may arise not only in the case where the annealing process is performed through the use of a plurality of laser light sources as described above but also in the case where the annealing process is performed through the use of a single laser light source.

Further, in Japanese Unexamined Patent Application Publication No. 2002-319606, in some cases (such as, for example, the case of a microcrystal with a particle diameter of a few tens of nm or less), the above-described characteristic state is not observed in a crystallized region. Therefore, in such a case, it is difficult to evaluate the degree of crystallization, so an evaluation method with higher precision is desired.

It is desirable to provide a method of forming a semiconductor thin film allowing the crystallinity degree of a semiconductor thin film formed through the use of crystallization by laser annealing to be evaluated with higher precision in the formation of the semiconductor thin film, and a semiconductor thin film inspection apparatus.

According to an embodiment of the invention, there is provided a method of forming a semiconductor thin film including the steps of: forming an amorphous semiconductor thin film on a substrate; forming a crystalline semiconductor thin film partially in each element region by applying laser light to the amorphous semiconductor thin film to selectively perform a heating process on the amorphous semiconductor thin film, thereby crystallizing the amorphous semiconductor thin film in a region irradiated with the laser light; and inspecting the crystallinity degree of the crystalline semiconductor thin film. Moreover, the step of inspecting includes the steps of determining a contrast between the luminance of a crystallized region and the luminance of a non-crystallized region by applying light to the crystalline semiconductor thin film and the amorphous semiconductor thin film, and performing screening of the crystalline semiconductor thin film on the basis of the determined contrast.

In the method of forming a semiconductor thin film according to the embodiment of the invention, after the amorphous semiconductor thin film is formed on the substrate, the laser light is applied to the amorphous semiconductor thin film to selectively perform the heating process on the amorphous semiconductor thin film, thereby the amorphous semiconductor thin film in the region irradiated with the laser light is crystallized thereby to form the crystalline semiconductor thin film partially in each element region. Then, after that, the crystallinity degree of the crystalline semiconductor thin film is inspected. In this case, in the step of inspecting, the contrast between the luminance of the crystallized region and the luminance of the non-crystallized region is determined by applying light to the crystalline semiconductor thin film and the amorphous semiconductor thin film, and screening of the crystalline semiconductor thin film is performed on the basis of the determined contrast. Thus, when screening of the crystalline semiconductor thin film is performed on the basis of the contrast between the luminance of the crystallized region and the luminance of the non-crystallized region, more reliable screening than ever before is achieved.

According to an embodiment of the invention, there is provided a semiconductor thin film inspection apparatus being a crystallinity degree inspection apparatus used for a crystalline semiconductor thin film, the crystalline semiconductor thin film being formed partially in each element region by applying laser light to an amorphous semiconductor thin film on an substrate to selectively perform a heating process on the amorphous semiconductor thin film, thereby crystallizing the amorphous semiconductor thin film in a region irradiated with the laser light. The semiconductor thin film inspection apparatus includes: a stage on which the substrate is mounted, the substrate including the crystalline semiconductor thin film formed thereon; a light source applying light to the crystalline semiconductor thin film and the amorphous semiconductor thin film; a derivation section determining a contrast between the luminance of a crystallized region and the luminance of a non-crystallized region on the basis of light emitted from the light source; and a screening section performing screening of the crystalline semiconductor thin film on the basis of the contrast determined by the derivation section.

In the semiconductor thin film inspection apparatus according to the embodiment of the invention, on the substrate on which the crystalline semiconductor thin film is formed partially in each element region, light is applied from the light source to the crystalline semiconductor thin film and the amorphous semiconductor thin film. Then, on the basis of the light emitted from the light source, the contrast between the luminance of the crystallized region and the luminance of the non-crystallized region is determined, and on the basis of the determined contrast, screening of the crystalline semiconductor thin film is performed. Since screening of the crystalline semiconductor thin film is performed on the basis of the contrast between the luminance of the crystallized region and the luminance of the non-crystallized region, more reliable screening than ever before is achieved.

In the method of forming a semiconductor thin film according to the embodiment of the invention, in the step of inspecting the crystallinity degree of the crystalline semiconductor thin film, light is applied to the crystalline semiconductor thin film and the amorphous semiconductor thin film, thereby the contrast between the luminance of the crystallized region and the luminance of the non-crystallized region is determined, and screening of the crystalline semiconductor thin film is performed on the basis of the determined contrast, so more reliable screening than ever before is achieved. Therefore, when the semiconductor thin film is formed through the use of crystallization by laser annealing, the crystallinity degree is evaluated with higher precision than ever before.

In the semiconductor thin film inspection apparatus according to the embodiment of the invention, light is applied from the light source to the crystalline semiconductor thin film and the amorphous semiconductor thin film, and the contrast between the luminance of the crystallized region and the luminance of the non-crystallized region is determined, and screening of the crystalline semiconductor thin film is performed on the basis of the determined contrast, so more reliable screening than ever before is achieved. Therefore, when the semiconductor thin film is formed through the use of crystallization by laser annealing, the crystallinity degree is evaluated with higher precision than ever before.

Other and further objects, features and advantages of the invention will appear more fully from the following description.

BRIEF DESCRIPTION OF THE DRAWINGS

FIG. 11 is an illustration for describing an evaluation technique according to the invention and evaluation techniques in related art.

FIGS. 12A and 12B are sectional views for describing an inspection step according to a modification 1 of the invention.

FIGS. 23A and 23B are schematic views for describing the correction process following FIGS. 22A to 22C.

FIG. 24 is an illustration of an example of a measurement image before the correction process according to the modification 9.

FIG. 25 is an illustration of an example of a corrected image after the correction process according to the modification 9.

DETAILED DESCRIPTION OF THE PREFERRED EMBODIMENTS

A preferred embodiment will be described in detail below referring to the accompanying drawings.

Figure 1:
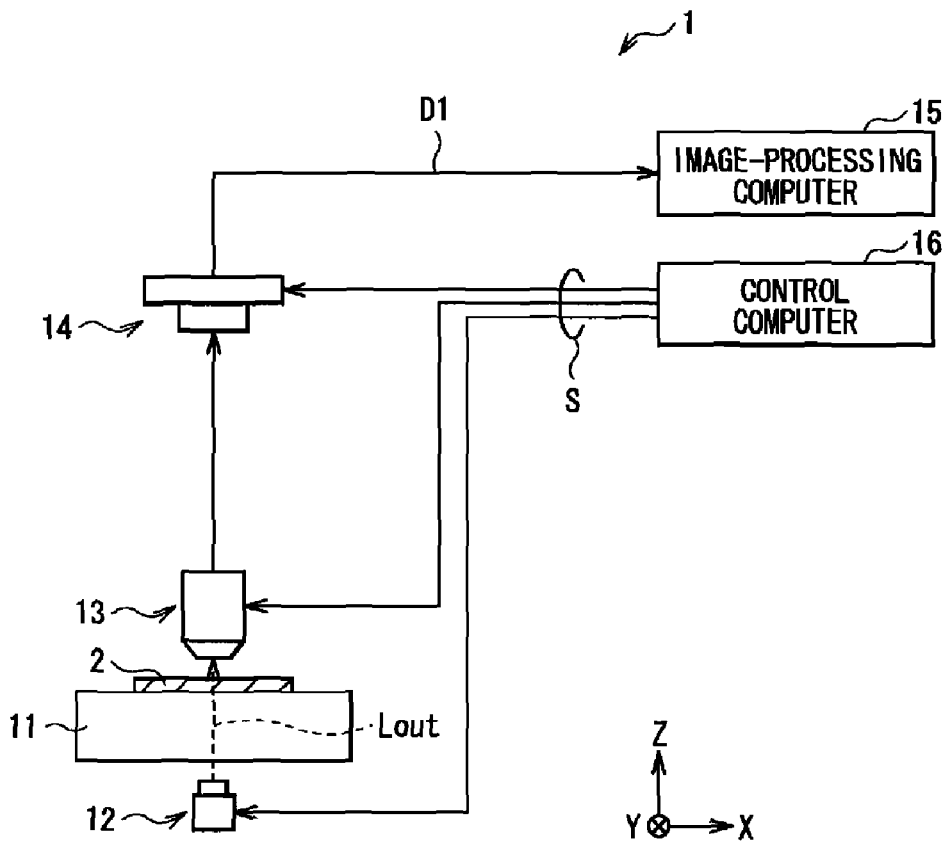
FIG. 1 is an illustration of the whole configuration of a semiconductor thin film inspection apparatus according to an embodiment of the invention.

FIG. 1 illustrates the whole configuration of a semiconductor thin film inspection apparatus (an inspection apparatus 1) according to an embodiment of the invention. The inspection apparatus 1 is used for, for example, a silicon semiconductor film formed during a step of manufacturing a thin film transistor having a bottom gate configuration (a bottom gate TFT). More specifically, the inspection apparatus 1 is a crystallinity degree inspection apparatus used for a Si (silicon) thin film substrate 2 (as will be described later, a substrate having a p-Si (polysilicon) film (a crystalline semiconductor thin film) which is formed partially in each element region (pixel) by forming an a-Si (amorphous silicon) film (an amorphous semiconductor thin film) on a transparent substrate, and then selectively applying laser light to the a-Si film to perform an anneal process on the a-Si film, thereby crystallizing an irradiated region (an irradiated region 41 which will be described later)). The inspection apparatus 1 includes a movable stage 11, an LED (Light Emitting Diode) 12, an objective lens 13, a CCD (Charge Coupled Device) camera 14, an image-processing computer 15 and a control computer 16. In the following description, as an example of a crystallized Si thin film, a p-Si film is used, but a microcrystalline Si film may be used.

On the movable stage 11, the Si thin film substrate as an object to be inspected is mounted (supported), and the movable stage 11 is arbitrarily movable in an X-axis direction or a Y-axis direction in the drawing in response to a control signal S supplied from the control computer 16 which will be described later. Moreover, the movable stage 11 is made of a material allowing light (irradiation light Lout) emitted from the LED 12 which will be described later to pass therethrough (for example, a glass plate) in the Si thin film substrate 2.

The LED 12 is a light source applying light (irradiation light Lout) to the Si thin film substrate 2 from the back side (a side opposite to a surface where the Si thin film substrate 2 is mounted) of the movable stage 11. As the irradiation light Lout, the LED 12 preferably applies green light as light with a wavelength region of approximately 500 to 600 nm as a central wavelength or monochromatic light with a wavelength region of approximately 500 to 600 nm, because unlike white light, green light or monochromatic light is not dependent on a spectrum distribution, so more universal measurement is performed. More specifically, in a white light source, a contrast value which will be described later may be changed because the spectrum distribution is different in the case where a plurality of measurement apparatuses are used, the case where a light source is replaced, or the like. On the other hand, in the case of a green light source or a monochromatic light source, it is not necessary to worry about such a change. In addition, instead of a high-luminance LED, a lamp of a microscope or the like may be used as the light source.

The objective lens 13 is an optical device for magnifying and detecting the irradiation light Lout (transmitted light) emitted from the LED 12 to pass through the movable stage 11 and the Si thin film substrate 2. Moreover, the CCD camera 14 is a camera highly sensitive to light with a wavelength region of approximately 500 to 600 nm, and includes a CCD image sensor as an image pickup device therein, thereby the CCD camera 14 picks up a transmission microscope image (a transmission image) of the a-Si film (the non-crystallized region) and the p-Si film (the crystallized region) in the Si thin film substrate 2.

The image-processing computer 15 performs screening of the p-Si film (performs an inspection process) on the basis of the transmission image of the a-Si film and the p-Si film obtained by the objective lens 13 and the CCD camera 14. More specifically, first, transmission image data D1 supplied from the CCD camera 14 is captured, and the image luminance of the transmission image data D1 is analyzed to determine a contrast between the transmission luminance of the p-Si film (the crystallized region) and the transmission luminance of the a-Si film (the non-crystallized region) formed on the Si thin film substrate 2, and on the basis of the determined contrast, the image-processing computer 15 performs screening to determine whether the p-Si film formed on the Si thin film substrate 2 is a conforming product or a defective product. The inspection process by the image-processing computer 15 will be described in detail later.

The control computer 16 performs lighting control of the irradiation light Lout by the LED 12, control of moving positions of the LED 12, the objective lens 13 and the CCD camera 14, switching control of the objective lens 13, and the like in response to the control signal S. Among them, regarding the control of the moving positions, the control computer 16 performs control for relatively displacing the LED 12, the objective lens 13 and the CCD camera 14 with respect to the Si thin film substrate 2 mounted on the movable stage 11.

Herein, the LED 12 corresponds to a specific example of "a light source" in the invention. Moreover, the objective lens 13, the CCD camera 14 and the image-processing computer 15 correspond to specific examples of "a derivation section" in the invention. The objective lens 13 and the CCD camera 14 correspond to specific examples of "an optical system of the derivation section" in the invention. The image-processing computer 15 corresponds to a specific example of "a screening section" in the invention. The control computer 16 corresponds to a specific example of "a control section" in the invention.

Figure 2:
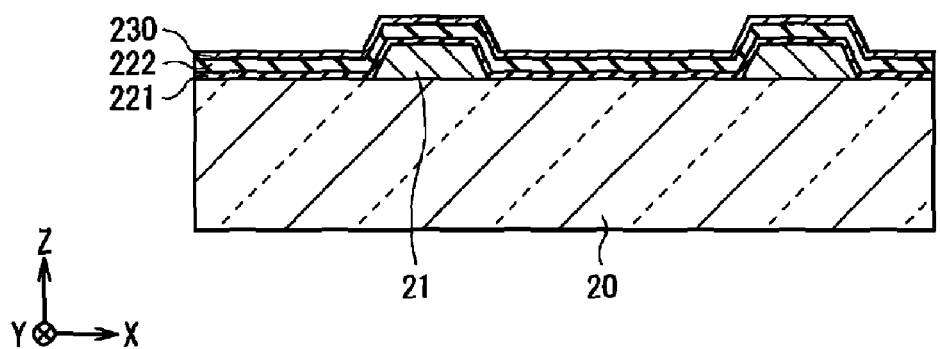
FIG. 2 is a sectional view illustrating a part of a main step of a method of forming a semiconductor thin film according to an embodiment of the invention.
Figure 3:
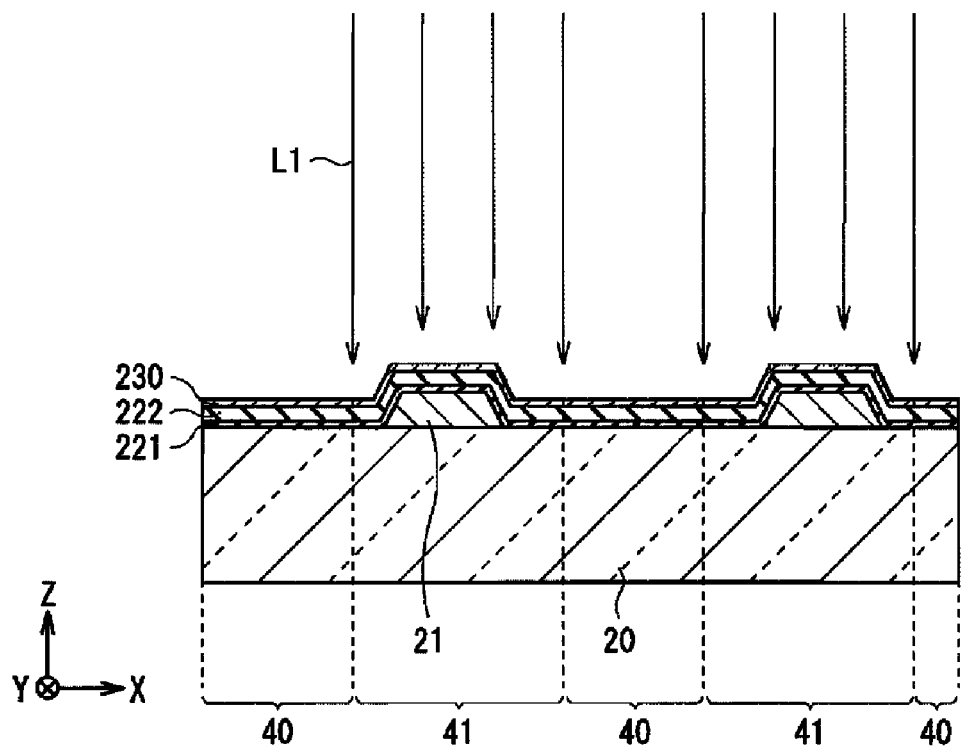
FIG. 3 is a sectional view illustrating a step following the step of FIG. 2.
Figure 4:
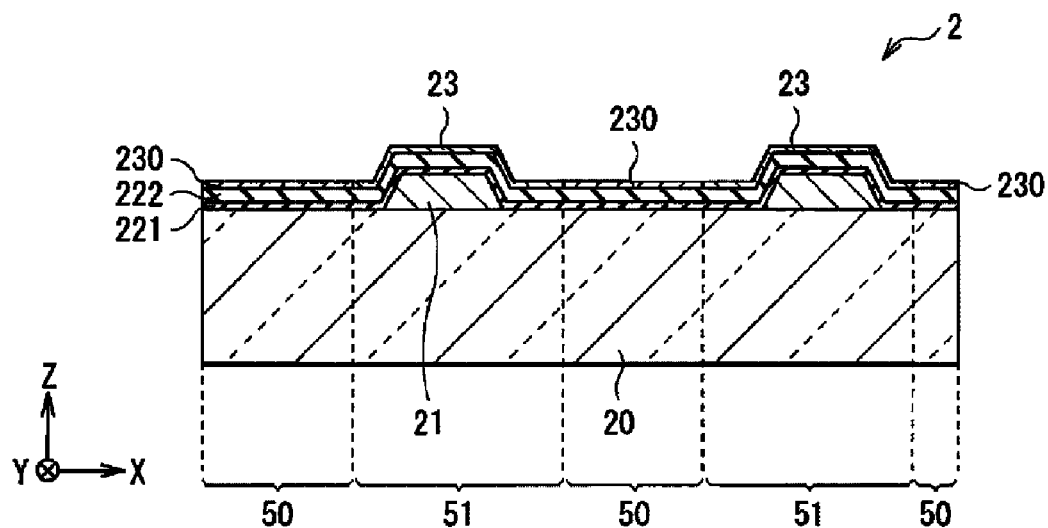
FIG. 4 is a sectional view illustrating a step following the step of FIG. 3.

Next, referring to FIGS. 2 to 10, a method of forming a semiconductor thin film according to an embodiment of the invention including an inspection step using the inspection apparatus 1 illustrated in FIG. 1 will be described below. FIGS. 2 to 4 illustrate sectional views (Z-X sectional views)

of a part of a main step of the method of forming a semiconductor thin film according to the embodiment. Moreover, FIG. 5 illustrates a flowchart of an example of the inspection step following the step of FIG. 4.

First, as illustrated in FIG. 2, for example, a gate electrode 21, gate insulating films 221 and 222 and an a-Si film 230 are formed in this order on a transparent substrate 20 (for example, with a substrate size of approximately 550 mm×650 mm) such as a glass substrate by, for example, a photolithography method. The gate electrode 21 is made of, for example, molybdenum (Mo), the gate insulating film 221 is made of, for example, silicon nitride ($SiN_X$), and the gate insulating film 222 is made of, for example, silicon oxide ($SiO_2$).

Next, as illustrated in FIG. 3, laser light L1 is partially applied to the a-Si film 230 on the transparent substrate 20 through the use of a laser diode light source (not illustrated) so as to selectively perform an annealing process (a heating process) on the a-Si film 230, thereby the a-Si film 230 is crystallized partially in each element region (corresponding to each pixel in the case where the Si thin film substrate 2 is applied to a display). More specifically, for example, as illustrated in FIG. 4, the annealing process is performed on an irradiated region 41 which is irradiated with the laser light L1 to crystallize the irradiated region 41, thereby the irradiated region 41 becomes a crystallized region 51 in which a p-Si film 23 is formed. On the other hand, the annealing process is not performed on a non-irradiated region 40 which is not irradiated with the laser light L1, thereby the non-irradiated region 40 is not crystallized to become a non-crystallized region 50 in which the a-Si film 230 is still formed.

Figure 5:
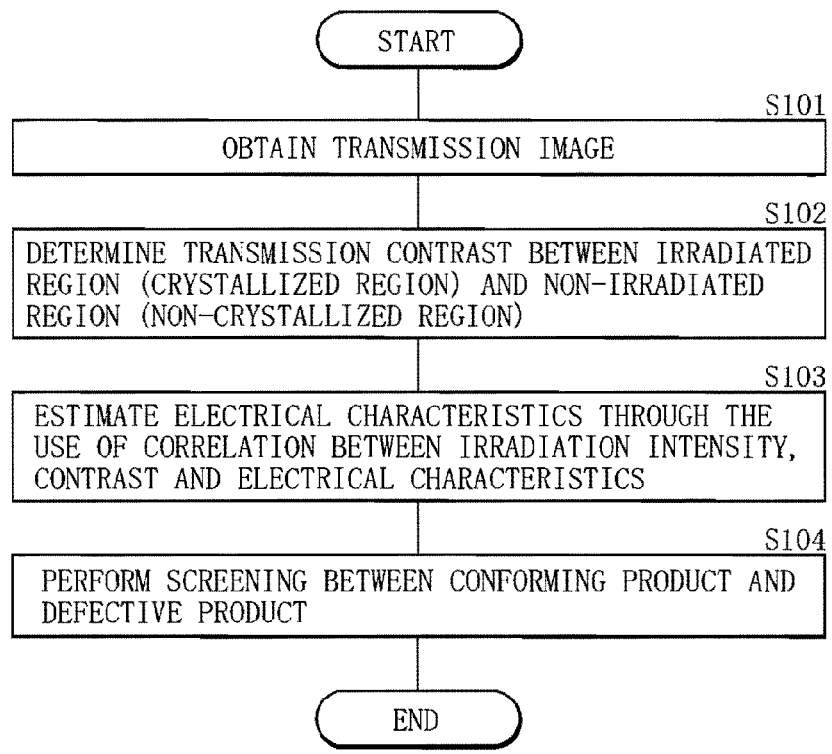
FIG. 5 is a flowchart illustrating an example of a step (an inspection step) following the step of FIG. 4.

Next, as illustrated in steps S101 to S104 in FIG. 5, an inspection of the crystallization state (crystallinity degree) of the p-Si film 23 formed on the transparent substrate 20 is performed by the inspection apparatus 1 illustrated in FIG. 1.

More specifically, first, the Si thin film substrate 2 on which the p-Si film 23 is formed is mounted on the moving stage 11, and the irradiation light Lout is applied to the p-Si film (the crystallized region 51) and the a-Si film (the non-crystallized region 50) by the LED 12 from the back side (a side opposite to a surface where the Si thin film substrate 2 is mounted) of the movable stage 11, and the objective lens 13 and the CCD camera 14 sense transmitted light passing through the movable stage 11 and the Si thin film substrate 2 to pick up an image, and then the image-processing computer 15 obtains a transmission image (transmission image data D1) of the p-Si film 23 (the crystallized region 51) and the a-Si film 230 (the non-crystallized region 50) (step S101 in FIG. 5). At this time, the LED 12, the objective lens 13 and the CCD camera 14 are relatively displaced with respect to the Si thin film substrate 2 mounted on the movable stage 11 in response to the control signal S supplied from the control computer 16, thereby transmission images at a plurality of points on the p-Si film 23 are obtainable.

Figure 6:
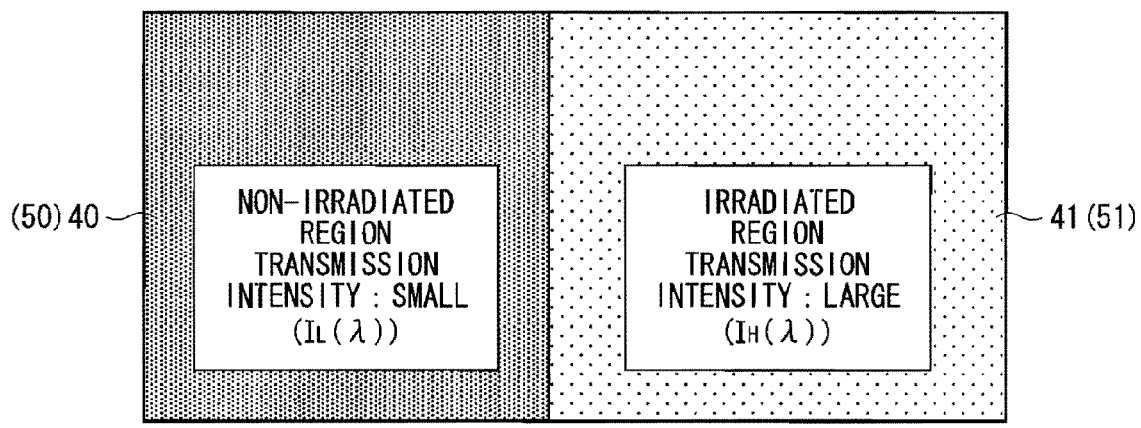
FIG. 6 is a schematic view for describing a laser light non-irradiated region and transmission characteristics of the non-irradiated region.

Next, the image-processing computer 15 determines a contrast (a transmission contrast) between the transmission luminance of the p-Si film 23 (the crystallized region 51) and the transmission luminance of the a-Si film 230 (the non-crystallized region 50) on the basis of obtained transmission image (the transmission image data D1) (step S102). The contrast is defined by the following expression (1-1) or (1-2). As the crystallinity degree of a Si film is heavily dependent on an energy density (irradiation intensity) in the annealing process, the transmittance of the Si film increases with the expansion of a crystallized region or an increase in crystal size. Therefore, for example, as illustrated in FIG. 6, the contrast is determined through the use of a difference between the transmission intensity (the transmission luminance) of the crystallized region 51 (the irradiated region 41) and the transmission intensity (the transmission luminance) of the non-crystallized region 50 (the non-irradiated region 40) (where the transmission intensity of the irradiated region 41 is $I_H(\lambda)$, and the transmission intensity of the non-irradiated region 40 is $I_L(\lambda)$). In addition, as the crystallized region 51, instead of the above-described p-Si film, a microcrystalline Si film may be used.

Mathematical Expression 1

$$\text{CONTRAST} = \frac{\left(\begin{array}{c}\text{AVERAGE LEVEL OF IRRADIATED REGION} - \\ \text{AVERAGE LEVEL OF NON-IRRADIATED REGION}\end{array}\right)}{\left(\begin{array}{c}\text{AVERAGE LEVEL OF IRRADIATED REGION} + \\ \text{AVERAGE LEVEL OF NON-IRRADIATED REGION}\end{array}\right)} \quad (1\text{-}1)$$

$$\text{CONTRAST} = \frac{\left(\begin{array}{c}\text{AVERAGE LEVEL OF IRRADIATED REGION} - \\ \text{AVERAGE LEVEL OF NON-IRRADIATED REGION}\end{array}\right)}{\text{AVERAGE LEVEL OF NON-IRRADIATED REGION}} \quad (1\text{-}2)$$

Figure 7A:
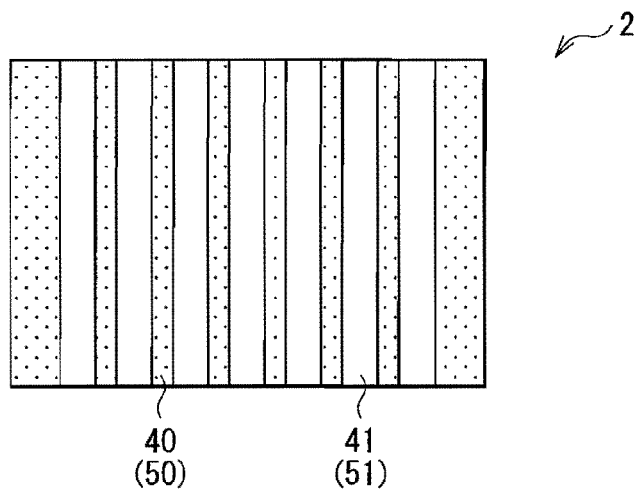
FIGS. 7A and 7B are schematic views for describing an expression for calculating contrast.

In this case, the above-described expression (1-1) is an expression for calculating a contrast called Michelson contrast. The Michelson contrast represents a contrast between the brightest white and the darkest black, and more specifically, for example, as illustrated in FIG. 7A, the Michelson contrast basically represents a contrast between regular sinusoidal bright and dark stripes. As the value of the contrast, by the definition in the expression, values of 0 to 1 (dimensionless quantity, no unit) are used, and the value of the contrast is represented by % contrast (0 to 100%) in many cases.

Figure 7B:
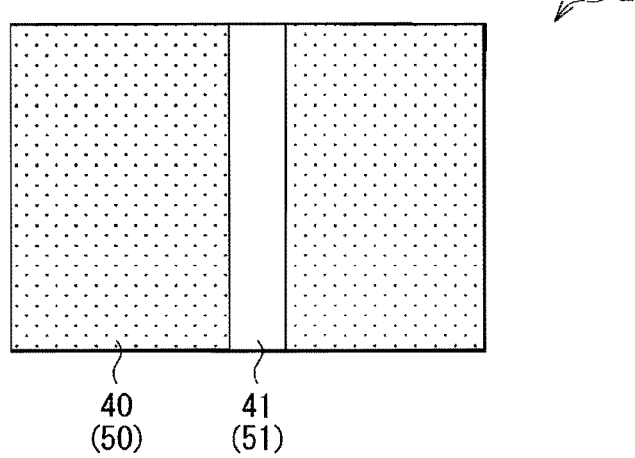

On the other hand, the above-described expression (1-2) is an expression for calculating a contrast called Weber contrast. For example, as illustrated in FIG. 7B, the Weber contrast is used in the case where a pattern with a clear edge is present in a uniform and wide background or the case where the light intensity of a background is substantially uniform.

Figure 8:
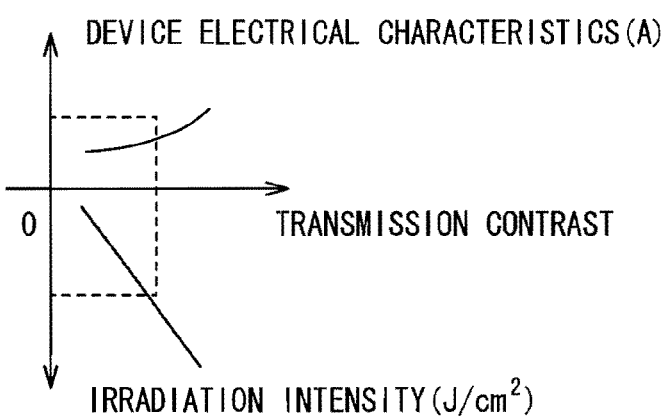
FIG. 8 is a plot illustrating an example of a correlation between irradiation intensity used in the inspection step illustrated in FIG. 5, contrast and electrical characteristics.

Next, for example, as illustrated in FIG. 8, on the basis of the determined transmission contrast, the image-processing computer 15 estimates electrical characteristics (device electrical characteristics; for example, a current value flowing between a source and a drain in a TFT) expected to be obtained in the p-Si film 23 through the use of a correlation between the transmission contrast, light irradiation intensity when obtaining the transmission image, and the electrical characteristics (step S103). A characteristic graph of the correlation as illustrated in FIG. 8 is preliminarily formed.

In this case, for example, in the case where variations in electrical characteristics between adjacent TFTs is as small as approximately 3% or less, for example, as illustrated in FIG. 8, the satisfaction of the following points (1) to (3) is demanded by an experimental result.

(1) The irradiation intensity and the transmission contrast have a relationship in which both of them increase substantially linearly (a proportional relationship).

(2) As the transmission contrast increases, the device electrical characteristics also increase.

(3) When the irradiation intensity is controlled so that the transmission contrast is constantly a specific value, the device electrical characteristics are also constant.

Moreover, in the case of a display using TFTs, typically, when a luminance difference between adjacent pixels is 3% or less, it is said that it is difficult to visually recognize the difference. In other words, when a current value difference between TFTs is 3% or less, the difference is not visually recognized. Therefore, for example, it is turned out that when a curve corresponding to the above-described point (2) is drawn preliminarily so that the differential coefficient of the curve is determined, and a contrast difference falls in a range of 0.03/the differential coefficient, a current value difference between the TFTs of 3% or less is achieved.

Figure 9:
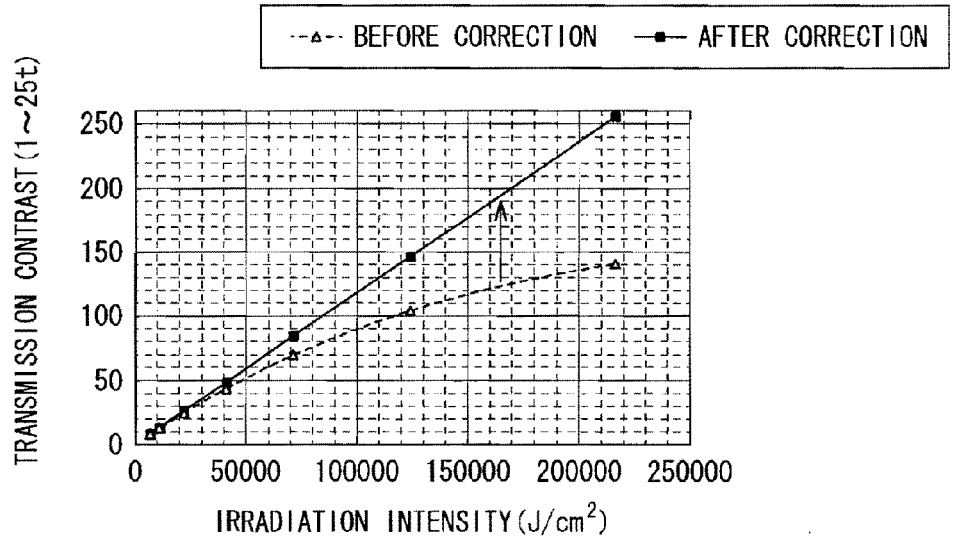
FIG. 9 is a plot for describing a method of correcting γ characteristics.
Figure 10:
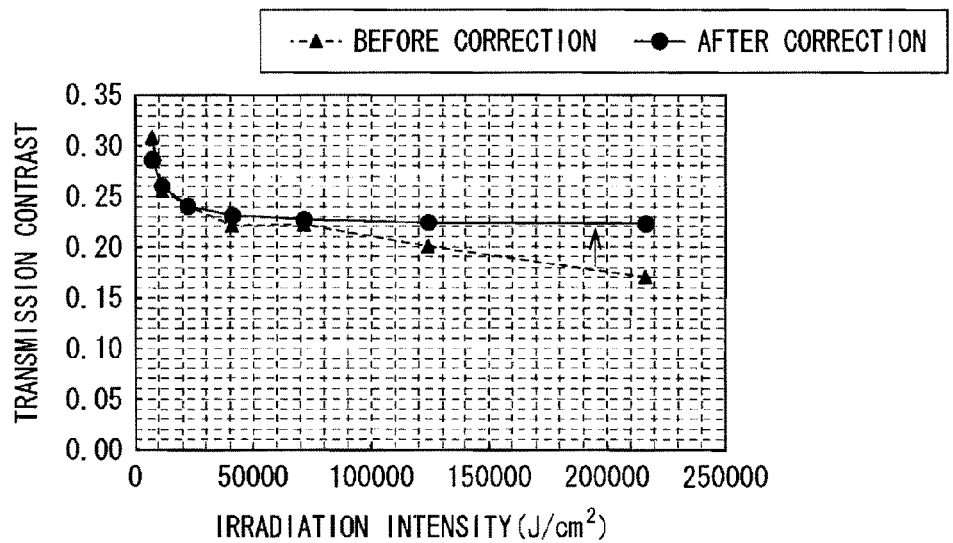
FIG. 10 is a plot for describing a change in correspondence relationship between irradiation intensity and contrast by correction of γ characteristics.

Further, at this time, for example, as illustrated in FIGS. 9 and 10, it is preferable for the image-processing computer 15 to correct γ characteristics between the irradiation intensity and the transmission contrast (characteristics of the CCD camera 14 or the like+transmittance characteristics of a material by light reaction) so that the γ characteristics V have a γ value=1. Alternatively, it is preferable to preliminarily use γ characteristics with a γ value=1 between the irradiation intensity and the transmission contrast, because when γ characteristics with a γ value=1 is used in such a manner, the evaluation of the crystallinity degree is allowed to be performed with higher precision. However, in the case where a wider dynamic range of irradiation intensity is desired, γ characteristics with a γ value=1 or less is preferably used.

More specifically, the following points (I) to (III) are true, where the transmission luminance level of the irradiated region 41 is A, the transmission luminance level of the non-irradiated region 40 is B, the transmission contrast is C, the transmission intensity is I, the transmittance is T, and a predetermined coefficient is K.

(I) In the case of γ=1 (in the case where the γ characteristics are linear characteristics)

In this case, the transmission contrast C represented by the following expression (4) is determined on the basis of a relational expression of the irradiated region 41 represented by the following expression (2) and a relational expression of the non-irradiated region 40 represented by the following expression (3). Then, the transmission contrast C in the expression (4) is not dependent on the transmission intensity I. Therefore, it is said that the transmission contrast C is not dependent on a light amount, so correction is not necessary.

Mathematical Expression 2

$$\begin{cases} KA = T_a \cdot I & (2) \\ KB = T_b \cdot I & (3) \end{cases}$$

$$C = \frac{T_a - T_b}{T_a + T_b} \quad (4)$$

(II) In the case of γ≠1 (in the case where the γ characteristics are γ-th characteristics)

In this case, the transmission contrast C represented by the following expression (7) is determined on the basis of a relational expression of the irradiated region 41 represented by the following expression (5) and a relational expression of the non-irradiated region 40 represented by the following expression (6). Then, the transmission contrast C in the expression (7) is not dependent on the transmission intensity I, so the transmission contrast C is not dependent on a light amount. However, it is said that depending on the γ value preliminarily determined, it is necessary to perform correction so that, for example, the γ characteristics have γ=1.

Mathematical Expression 3

$$\begin{cases} KA = K(T_a \cdot I^\gamma) & (5) \\ KB = K(T_b \cdot I^\gamma) & (6) \end{cases}$$

$$C = \frac{T_a^\gamma - T_b^\gamma}{T_a^\gamma + T_b^\gamma} \quad (7)$$

(III) In the case of γ≠1 (in the case where the γ characteristics are γ-th characteristics, and the γ characteristics of the non-irradiated region 40 differ from the γ characteristics of the irradiated region 41 (the γ values are different from each other))

In this case, the transmission contrast C represented by the following expression (10) is determined by a relational expression of the irradiated region 41 represented on the basis of the following expression (8) and a relational expression of the non-irradiated region 40 represented by the following expression (9). The transmission contrast C in the expression (10) is dependent on the transmission intensity I, so the transmission contrast C is dependent on a light amount. Therefore, it is said that depending on the γ value preliminarily determined and a light amount in measurement, it is necessary to perform correction so that, for example, the γ characteristics have γ=1.

Mathematical Expression 4

$$\begin{cases} KA = K_a(T_a \cdot I)^{\gamma a} & (8) \\ KB = K_b(T_b \cdot I)^{\gamma b} & (9) \end{cases}$$

$$C = \frac{K_a \cdot T_a^{\gamma a} - K_b \cdot T_b^{\gamma b} \cdot I^{(\gamma b - \gamma a)}}{T_a^{\gamma a} + T_b^{\gamma b} \cdot I^{(\gamma b - \gamma a)}} \quad (10)$$

Next, through the use of the correlation between the transmission contrast, the irradiation intensity and the device electrical characteristics as illustrated in, for example, FIG. 8, the image-processing computer 15 performs screening of the p-Si film 23 (screening to determine whether the p-Si film 23 is a conforming product or a defective product) (step S104). More specifically, on the basis of the expected value of the device electrical characteristics in the step S103, screening to determine whether the p-Si film 23 is a conforming product or a defective product is performed. Thereby, the crystallinity degree inspection process on the p-Si film 23 formed on the transparent substrate 20 is completed.

Thus, in the embodiment, the a-Si film 230 is formed on the transparent substrate 20, and then the laser light L1 is partially applied to the a-Si film 230 to selectively perform the annealing process (the heating process) on the a-Si film 230, thereby the a-Si film 230 in the irradiated region 41 is crystallized so that the p-Si film 23 is formed partially in each element region (pixel). Then, after that, the crystallinity degree of the p-Si film 23 is inspected by the inspection apparatus 1 (an inspection process is performed). In this case, in the inspection process, the irradiation light Lout is applied to the p-Si film 23 and the a-Si film 230 by the LED 12 from the back side of the movable stage 11 on which the transparent substrate 20 (the Si thin film substrate 2) having the p-Si film 23 and the a-Si film 230 formed thereon is mounted, and transmitted light passing through the movable stage 11 and the p-Si film 23 or the a-Si film 230 is sensed by the CCD camera 14 through the objective lens 13, thereby the transmission image of the p-Si film 23 and the a-Si film 230 (the transmission image data D1) is obtained. Then, in the image-processing computer 15 obtaining the transmission image data D1, the transmission contrast between the transmission luminance of the p-Si film 23 (the crystallized region 51) and the transmission luminance of the a-Si film 230 (the non-crystallized region 50) is determined, and screening of the p-Si film 23 is performed on the basis of the determined transmission contrast. Thus, when screening of the p-Si film 23 is performed on the basis of the transmission contrast between the transmission luminance of the crystallized region 51 and the transmission luminance of the non-crystallized region 50, more reliable screening than ever before is achieved (for example, even in the case of a microcrystalline Si film with a particle diameter of a few tens of nm or less, or the like, reliable screening is performed).

Moreover, when screening is performed on the basis of such a transmission contrast, for example, as illustrated in FIG. 11, compared to a spectroscopic ellipsometry method, a Raman spectroscopy method, a SEM (Scanning Electron Microscope) method and a TEM (Transmission Electron Microscope) method as evaluation techniques in related art, evaluation is achieved at extremely higher speed, and a non-contact and nondestructive inspection of a microscopic region is achieved, and a numerical quantification may be performed.

As described above, in the embodiment, in the crystallinity degree inspection process on the p-Si film 23, the irradiation light Lout is applied to the p-Si film 23 and the a-Si film 230 by the LED 12, thereby the transmission image of the p-Si film 23 and the a-Si film 230 (the transmission image data D1) is obtained, and in the image-processing computer 15, the transmission contrast between the transmission luminance of the p-Si film 23 (the crystallized region 51) and the transmission luminance of the a-Si film 230 (the non-crystallized region 50) is determined, and screening of the p-Si film 23 is performed on the basis of the determined transmission contrast, so more reliable screening than ever before is achieved. Therefore, in the formation of the Si thin film through the use of crystallization by laser annealing, the crystallinity degree of the Si thin film is evaluated with higher precision than ever before (for example, in the case where the gray level of the CCD camera 14 is 12 bits, evaluation may be performed with a precision of 1/4096). Therefore, even in the case where a small difference in laser beam diameter due to a small difference in focal point position or a difference in divergence angle, a difference in power density on an object to be irradiated with the irradiation light Lout (the a-Si film 230) caused by a small aberration in an optical system, or the like occurs, crystallization by the laser diode in the annealing process is controllable. Moreover, a difference in crystal particle size or other characteristic between irradiated regions on the p-Si film 23 is reduced. Further, a noncontact and nondestructive crystallinity degree inspection is performed on the Si thin film substrate 2, so crystallization monitoring with high reproducibility is performed for a short time.

More specifically, screening of the p-Si film 23 is performed through the use of the correlation between the determined transmission contrast, the irradiation intensity of light when obtaining the transmission image and the electrical characteristics expected to be obtained in the p-Si film 23, so the above-described effects are obtained.

Moreover, compared to the evaluation techniques in related art, evaluation is achieved at extremely high speed, so real-time measurement may be performed. Therefore, a real-time feedback may be performed while performing the annealing process.

Further, the transmission image of the p-Si film 23 and the a-Si film 230 (the transmission image data D1) is obtained on the basis of the transmitted light of the irradiation light Lout, and the contrast (the transmission contrast) is determined on the basis of the transmission image, so compared to the case where a reflection image which will be described later is used, evaluation may be performed with higher precision.

In the case where the γ characteristics with a γ value=1 between the irradiation intensity and the transmission contrast is preliminarily used, or the case where the γ characteristics between the irradiation intensity and the transmission contrast is corrected so as to have a γ value=1, crystallinity degree evaluation may be performed with higher precision. On the other hand, in the case where the γ characteristics with a γ value=1 or less between the irradiation intensity and the transmission contrast is used, the dynamic range of irradiation intensity may be expanded.

As a monochromatic wavelength light source (green light source) is used, evaluation may be performed with higher precision, compared to the case where a multiwavelength light source is used. More specifically, in the case where the monochromatic wavelength light source is used, for example, a transmission contrast CNT represented by the following expression (13) is determined on the basis of the transmission intensity $I_H(\lambda)$ of the irradiated region 41 represented by the following expression (11) and the transmission intensity $I_L(\lambda)$ of the non-irradiated region 40 represented by the following expression (12). Then, the transmission contrast CNT in the expression (13) is not dependent on the transmission intensity $I_H(\lambda)$ and the transmission intensity $I_L(\lambda)$, so the transmission contrast CNT is not affected by the spectrum distribution of the light source, and measurement evaluation may be performed with higher precision. On the other hand, in the case where the multiwavelength light source is used, for example, a transmission contrast CNT represented by the following expression (16) is determined on the basis of power $P_H$ in the irradiated region 41 represented by the following expression (14) and power $P_L$ in the non-irradiated region 40 represented by the following expression (15). Then, the transmission contrast CNT in the expression (16) is dependent on the power $P_H$ and the power $P_L$, so the transmission contrast CNT is affected by the spectrum distribution of the light source.

Mathematical Expression 5

$$\begin{cases} I_H(\lambda) = Io(\lambda) \times \exp(-\alpha_H(\lambda) \cdot d) = Io(\lambda) \times T_H(\lambda) & (11) \\ I_L(\lambda) = Io(\lambda) \times \exp(-\alpha_L(\lambda) \cdot d) = Io(\lambda) \times T_L(\lambda) & (12) \end{cases}$$

$$CNT = (I_H(\lambda) - I_L(\lambda))/(I_H(\lambda) + I_L(\lambda)) \qquad (13)$$
$$(T_H(\lambda) - T_L(\lambda))/(T_H(\lambda) + T_L(\lambda))$$

Mathematical Expression 6

$$\begin{cases} P_H = \int d\lambda \cdot I_H(\lambda) = \int d\lambda \cdot Io(\lambda) \times T_H(\lambda) & (14) \\ P_L = \int d\lambda \cdot I_L(\lambda) = \int d\lambda \cdot Io(\lambda) \times T_L(\lambda) & (15) \end{cases}$$

$$CNT = (P_H(\lambda) - P_L(\lambda))/(P_H(\lambda) + P_L(\lambda)) \qquad (16)$$

When the transmission image of the p-Si film 23 and the a-Si film 230 (the transmission image data D1) is obtained, green light is used as light (the irradiation light Lout) applied to the p-Si film 23 and the a-Si film 230, so more universal measurement may be performed.

In the case where in the annealing process, the laser light L1 is applied through the use of a plurality of laser light sources, the annealing process may be performed for a short time by improving the throughput of the annealing process. Further, even in the case where a plurality of laser light sources are used in such a manner, when the above-described inspection process is performed, an influence of variations in the intensity of laser light may be prevented, and in-plane variations in the characteristics of the p-Si film 23 may be reduced.

The LED 12, the objective lens 13 and the CCD camera 14 are relatively displaced with respect to the Si thin film substrate 2 mounted on the movable stage 11 in response to the control signal S supplied from the control computer 16, so transmission images at a plurality of points on the p-Si film 23 and the a-Si film 230 are obtained, and inspection may be performed at such a plurality of points.

Now, some modifications of the invention will be described below. Like components are denoted by like numerals as of the embodiment and will not be further described.

Modification 1

FIG. 12B is a sectional view (a Z-X sectional view) for describing an inspection process according to a modification 1. In the modification, the laser light L1 is applied to a light-absorbing layer 231 on the a-Si film 230 in a step of forming the p-Si film 23, thereby a heating process is performed indirectly on the a-Si film 230. In other words, in the above-described embodiment, for example, as illustrated in FIG. 12A, the laser light L1 is applied to the a-Si film 230 in the step of forming the p-Si film 23, thereby the heating process is performed directly on the a-Si film 230. On the other hand, in the modification, the heating process is performed indirectly on the a-Si film 230.

In the modification, measurement in a state in which the light-absorbing layer 231 is still laminated may be performed. In other words, transmittance shows a strong correlation between before and after the removal of the light-absorbing layer 231, so when a corresponding table is formed preliminarily, the value of the contrast may be estimated without removing the light-absorbing layer 231.

Moreover, it should be noted that in FIGS. 12A and 12B, in the case where light concurrently passes through two layers, that is, the light-absorbing layer 231 and the pattern of the gate electrode 21, the transmission intensity becomes 0, thereby it is difficult to perform evaluation.

Modifications 2 and 3

Figure 13:
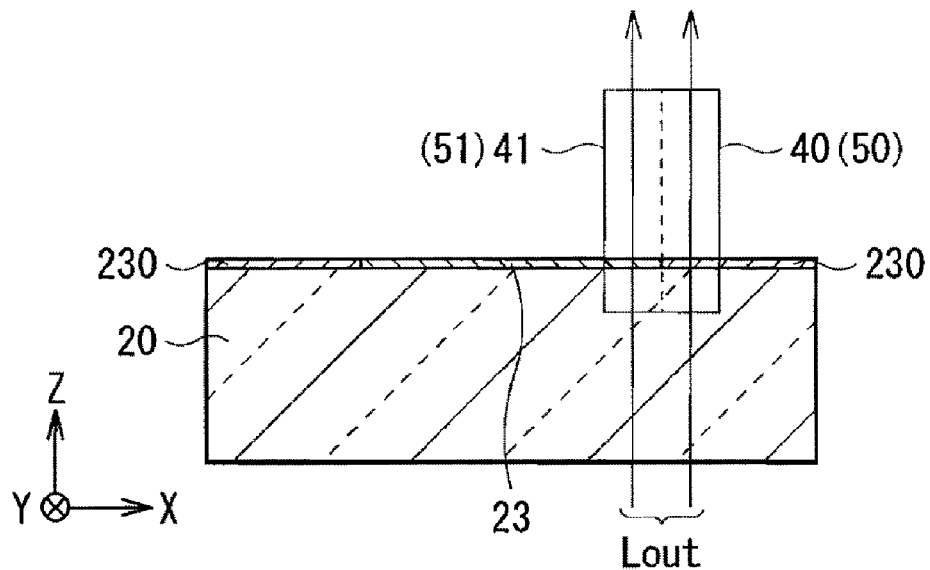
FIG. 13 is a sectional view for describing an inspection step according to a modification 2 of the invention.
Figure 14:
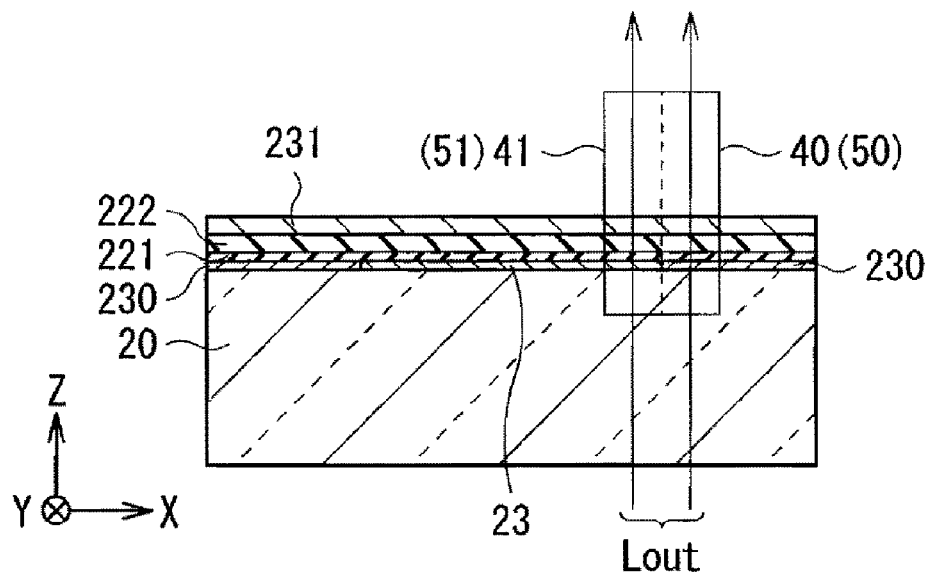
FIG. 14 is a sectional view for describing an inspection step according to a modification 3 of the invention.

FIG. 13 is a sectional view (a Z-X sectional view) for describing an inspection step according to a modification 2. Moreover, FIG. 14 is a sectional view (a Z-X sectional view) for describing an inspection step according to a modification 3. The modifications 2 and 3 correspond to an evaluation method in a step of manufacturing a thin film transistor with a top gate configuration (a top gate TFT). In the modification 3, as in the case of the above-described modification 1, a heating process is performed indirectly on the a-Si film 230 through the use of the light-absorbing layer 231.

Also in the modifications 2 and 3, it should be noted that in the case where light concurrently passes through two layers, that is, the light-absorbing layer 231 and the pattern of the gate electrode 21, the transmission intensity becomes 0, thereby it is difficult to perform evaluation.

Modifications 4 to 6

Figure 15:
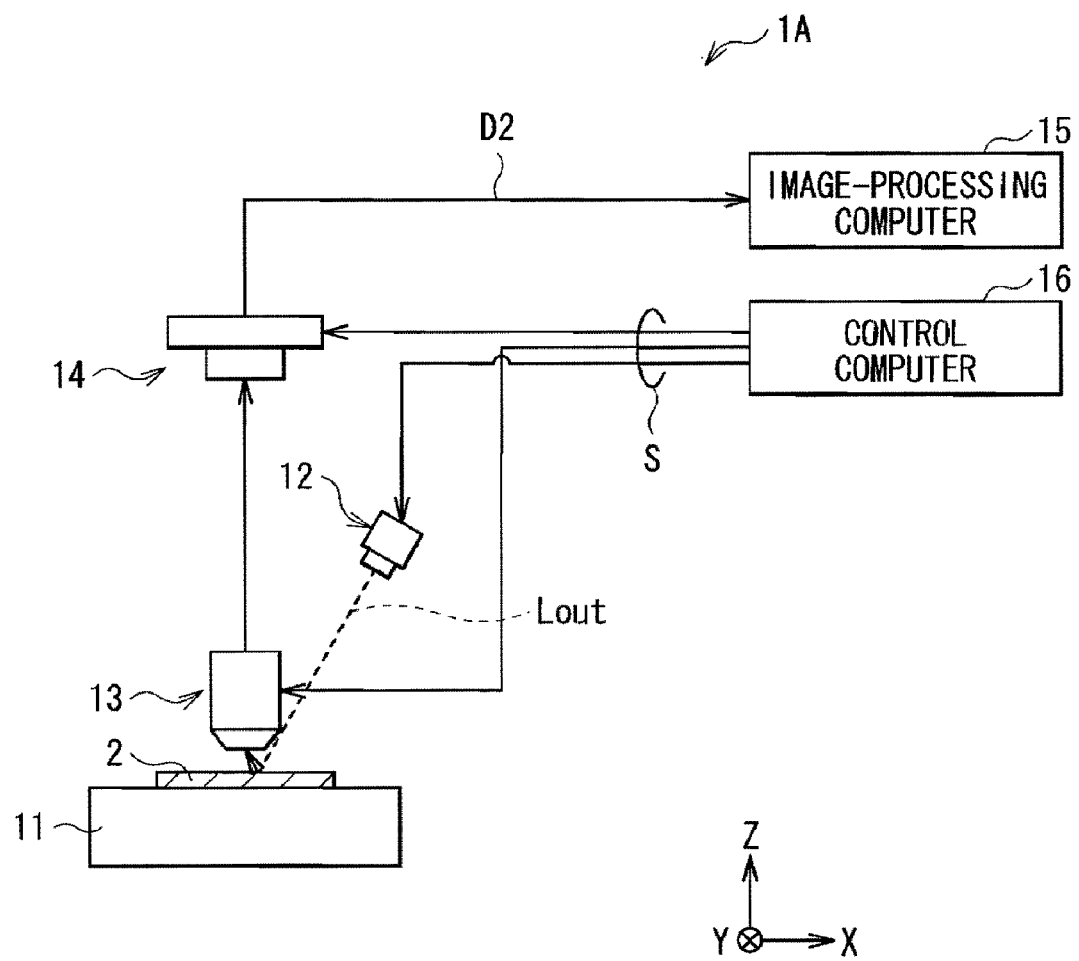
FIG. 15 is an illustration of the whole configuration of a semiconductor thin film inspection apparatus according to modifications 4 to 6 of the invention.

FIG. 15 illustrates the whole configuration of a semiconductor thin film inspection apparatus (an inspection apparatus 1A) according to modifications 4 to 6. In the inspection apparatus 1A, a reflection image of the p-Si film 23 and the a-Si film 230 (reflection image data D2) is obtained on the basis of reflected light of the irradiation light Lout, and a contrast (a reflection contrast: a contrast between the reflection luminance of the p-Si film 23 (the crystallized region 51) and the reflection luminance of the a-Si film 230 (the non-crystallized region 50)) is determined on the basis of the reflection image.

Then, screening of the p-Si film 23 is performed on the basis of the determined reflection contrast. To determine such a reflection contrast, as in the case of the transmission contrast, the above-described expression (1-1) or (1-2) may be used. In addition, the LED 12 may be arranged above the movable stage 11, and the irradiation light Lout from the LED 12 is applied to the Si thin film substrate 2 through a beam splitter (not illustrated).

Figure 16:
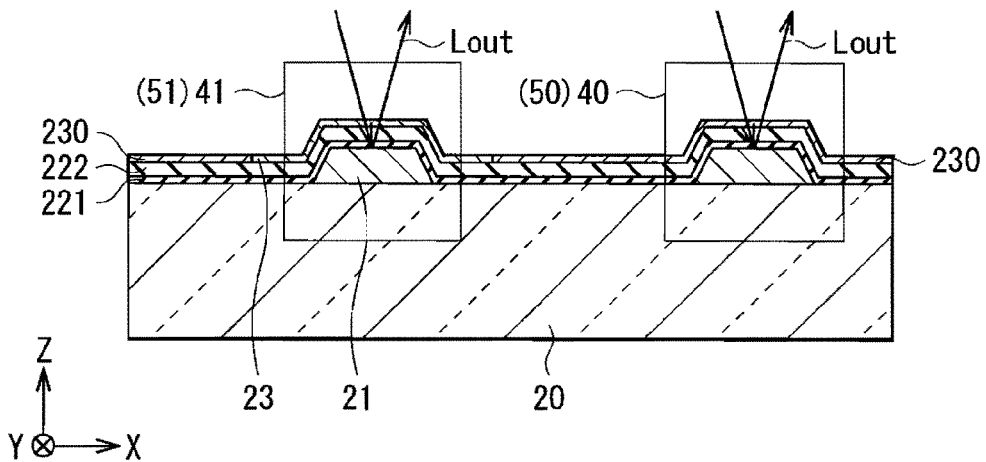
FIG. 16 is a sectional view for describing an inspection step according to the modification 4 of the invention.
Figure 17:
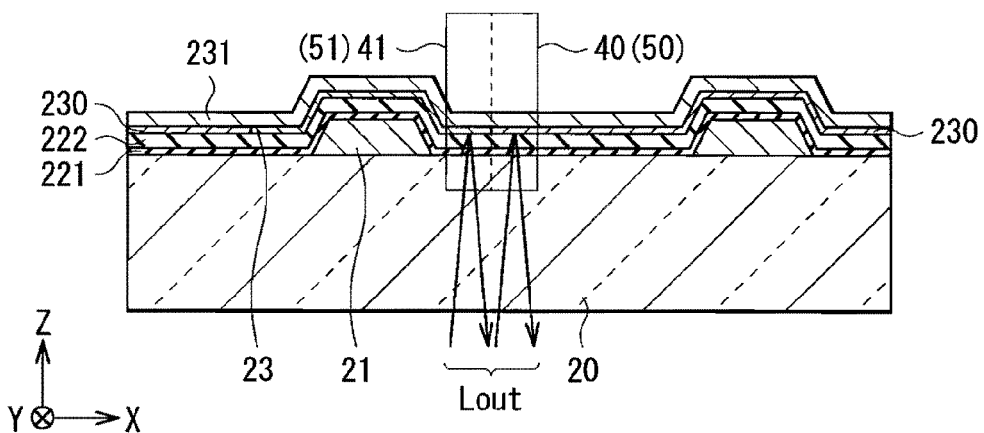
FIG. 17 is a sectional view for describing an inspection step according to the modification 5 of the invention.
Figure 18:
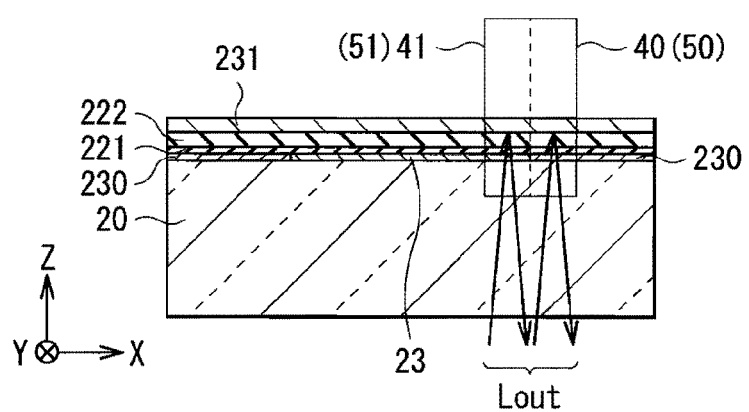
FIG. 18 is a sectional view for describing an inspection step according to the modification 6 of the invention.

For example, in the modification 4 illustrated in FIG. 16, the inspection apparatus 1A is used for evaluation during a step of manufacturing the bottom gate TFT by a direct heating method. For example, in the modification 5 illustrated in FIG. 17, the inspection apparatus 1A is used for evaluation during a step of manufacturing the bottom gate TFT by an indirect heating method. For example, in the modification 6 illustrated in FIG. 18, the inspection apparatus 1A is used for evaluation during a step of manufacturing the top gate TFT by an indirect heating method.

Thus, in the case where screening of the p-Si film 23 is performed on the basis of the reflection contrast, sensitivity is lower than that in the case where the transmission contrast described in the above-described embodiment or the like is used. However, crystallinity on a base pattern (in the case of a bottom gate, a gate pattern) may be evaluated by evaluation with a light source with a wavelength region of blue light or less. Moreover, in the case where screening of the p-Si film 23 is performed on the basis of the reflection contrast, the sensitivity may be improved more by a shorter-wavelength light source. In particular, in the case where E1 (280 nm) or E2 (370 nm) is used, a difference in reflectivity between the irradiated region 41 and the non-irradiated region 40 may be increased.

It should be noted that even in the modifications 4 to 6, in the case where light concurrently passes through two layers, that is, the light-absorbing layer 231 and the pattern of the gate electrode 21, the transmission intensity becomes 0, thereby it is difficult to perform evaluation.

Modifications 7 and 8

Figure 19:
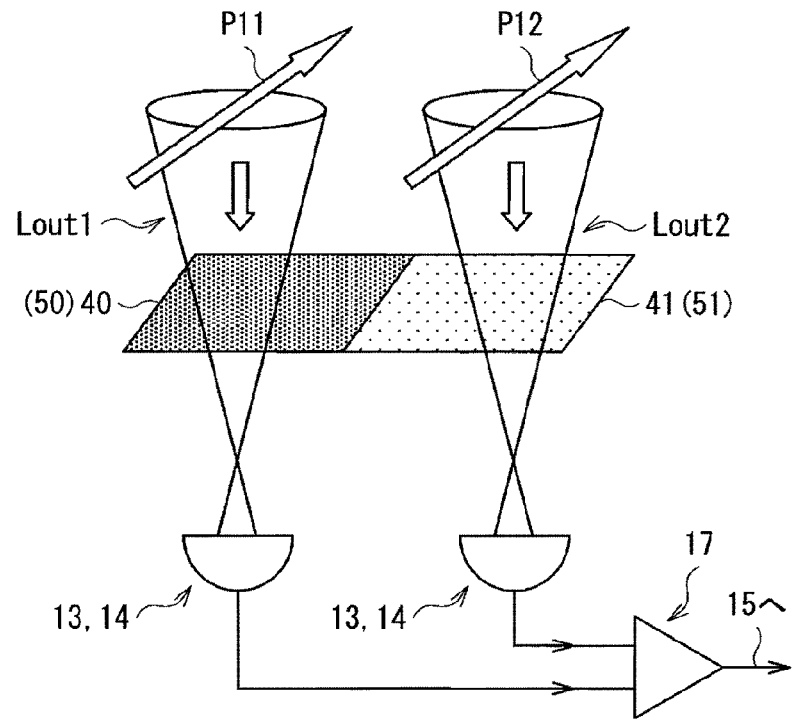
FIG. 19 is a schematic view for describing an inspection step according to a modification 7 of the invention.
Figure 20:
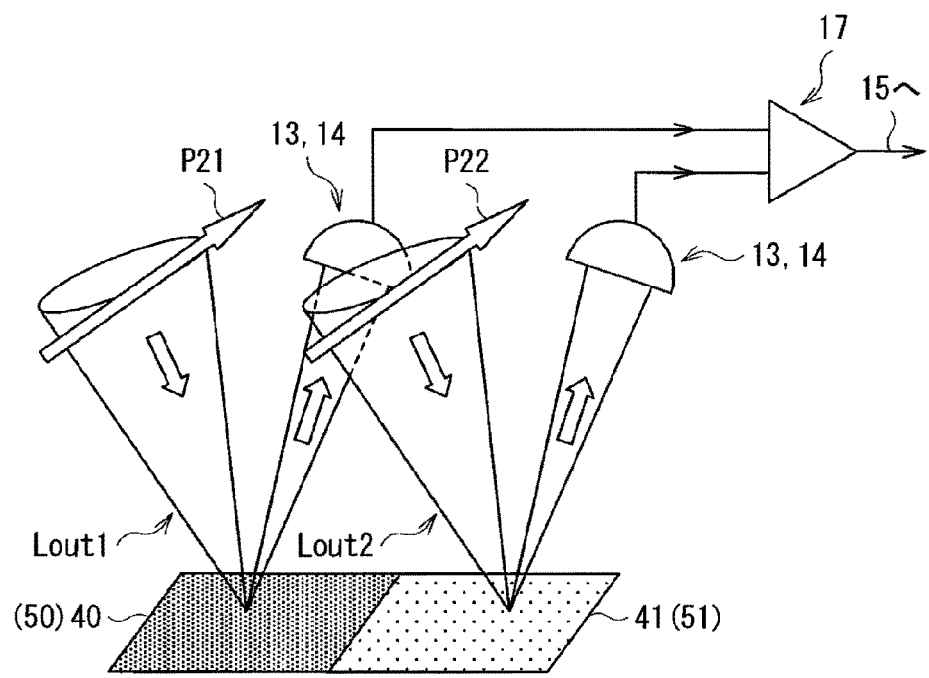
FIG. 20 is a schematic view for describing an inspection step according to a modification 8 of the invention.

FIG. 19 is a schematic view for describing an inspection step according to a modification 7. FIG. 20 is a schematic view for describing an inspection step according to a modification 8. In the modifications 7 and 8, in a step of determining a contrast, the irradiation light Lout is divided into a plurality of beams (for example, two beams, that is, irradiation light Lout1 and irradiation light Lout2), and the luminance of the crystallized region 51 and the luminance of the non-crystallized region 50 are differentially amplified by a differential amplifier 17, and then the contrast is determined. In the modification 7, screening of the p-Si film 23 is performed on the basis of the transmission contrast, and in the modification 8, screening of the p-Si film 23 is performed on the basis of the reflection contrast.

In such modifications 7 and 8, the transmitted light intensity or reflection intensity is differentially amplified, thereby measurement evaluation may be performed by high-precision and high-speed scanning (for example, scanning in directions indicated by arrows P11, P12, P21 and P22 in FIGS. 19 and 20).

Modification 9

Figure 21A:
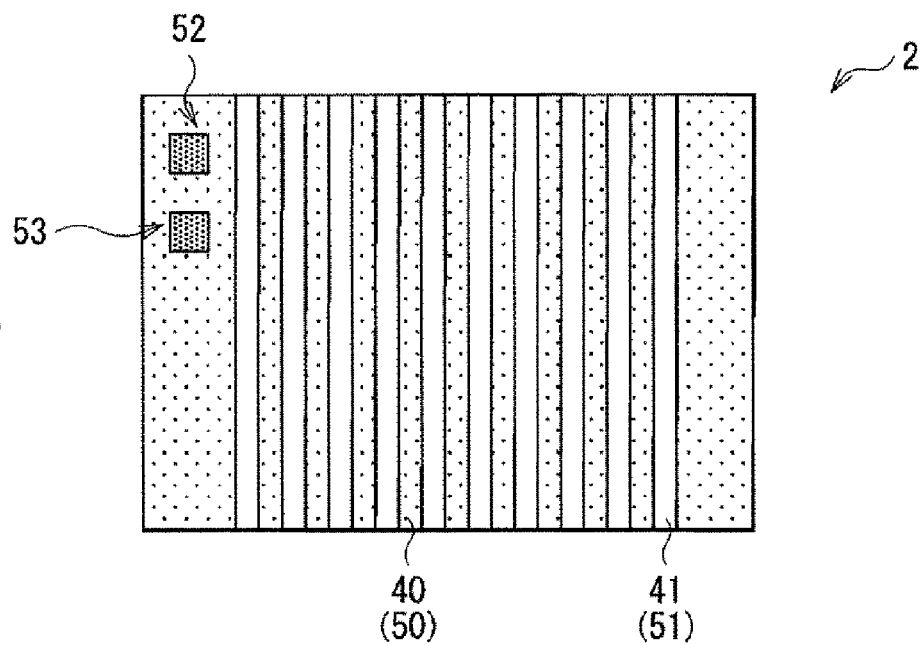
FIGS. 21A and 21B are schematic views for describing an inspection step according to a modification 9 of the invention.
Figure 21B:
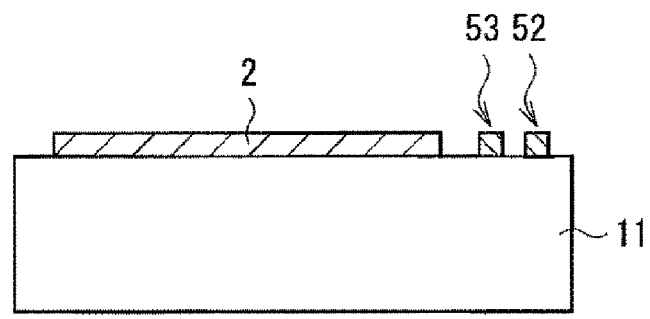

FIGS. 21A and 21B are illustrations for describing an inspection step according to a modification 9, and FIG. 21A illustrates a plane configuration example of the Si thin film substrate 2 used in the inspection step in the modification, and FIG. 21B illustrates side configuration examples of the movable stage 11 and the Si thin film substrate 2 used in the inspection step in the modification.

As illustrated in FIGS. 21A and 21B, in the modification, a reference level measurement region 52 and a zero measurement region 53 are preliminarily arranged in predetermined positions on the Si thin film substrate 2 (the transparent substrate 20) (refer to FIG. 21A) or on the movable stage 11 on which the Si thin film substrate 2 is mounted (refer to FIG. 21B).

The reference level measurement region 52 is a measurement region for obtaining a reference image with respect to a picked-up image (the transmission image or the reflection image) on the basis of the irradiation light Lout. On the other hand, the zero level measurement region 53 is a measurement region for obtaining a zero level image corresponding to an offset component when obtaining the picked-up image and the reference image on the basis of the irradiation light Lout.

Thereby, in the inspection step in the modification, when the transmission contrast or the reflection contrast is calculated by the above-described expression (1-1) or (1-2) (corresponding to the step S102 in FIG. 5), correction is performed on a luminance distribution of the obtained picked-up image by, for example, the following expression (17), and then these contrasts are determined.

(luminance distribution of picked-up image after correction)={(luminance distribution of picked-up image before correction−luminance distribution of zero level image)/(luminance distribution of reference image−luminance distribution of zero level image)}×{average value of (luminance distribution of reference image−luminance distribution of zero level image)}  (17)

More specifically, in the inspection step in the modification, for example, as illustrated in FIGS. 22A, 22B, 22C, 23A and 23B, correction is performed on the luminance distribution of the obtained picked-up image in the image-processing computer 15.

Figure 22A:
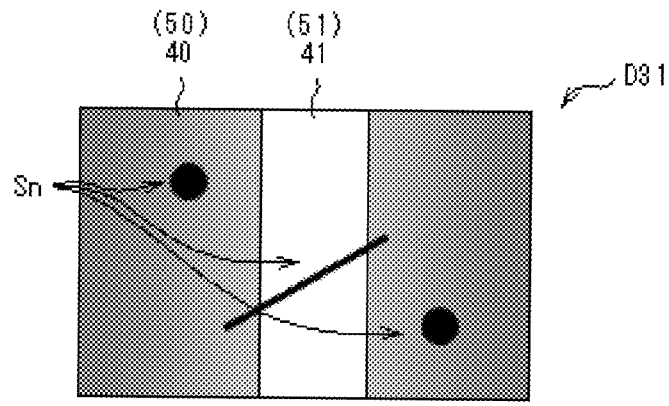
FIGS. 22A to 22C are schematic views for describing an example of a correction process according to the modification 9 of the invention.

In other words, first, as illustrated in FIG. 22A, in a region subjected to evaluation, a picked-up image (a measurement image; measurement image data D31) of the irradiated region 41 (the crystallized region 51) and the non-irradiated region 40 (the not-crystallized region 50) is obtained. As illustrated in the drawing, the measurement image is in state in which noises Sn (noises by an optical system (such as flaws or dust), light intensity unevenness of the light source, and the like) are included.

Figure 22B:
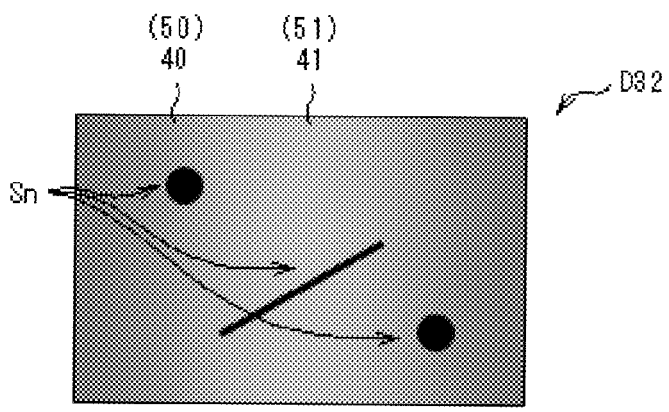

Next, as illustrated in FIG. 22B, in the reference level measurement region 52, the above-described reference image (reference image data D32) is obtained. As illustrated in the drawing, the reference image is in a state in which the noises Sn common to the above-described obtained measurement image are included.

Figure 22C:
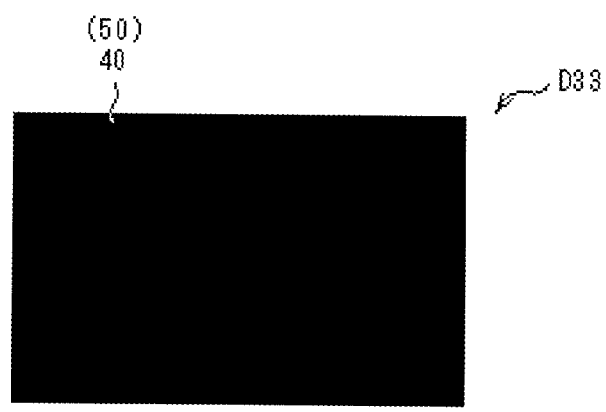

Next, as illustrated in FIG. 22C, in the zero level measurement region 53, the zero level image (zero level image data D33) is obtained. In other words, an image in which the light intensity is zero is obtained in order to remove an influence of the offset component such as a dark current.

Next, as illustrated in FIG. 23A, through the use of the following expressions (18) and (19), the obtained zero level image is subtracted from each of the measurement image and the reference image which are obtained in the above-described manner so as to perform zero level correction. Thereby, the influence of the offset component such as a dark current is removed from the measurement image and the reference image.

Measurement image data $D31a$ obtained after zero level correction=$D31$-$D33$  (18)

Reference image data $D32a$ obtained after zero level correction=$D32$-$D33$  (19)

Then, as illustrated in FIG. 23B, the above-described expression (17) and the following expression (20), the measurement image obtained after above-described zero level correction is divided by luminance per pixel of the reference image obtained after zero level correction, then multiplied by the average value of the luminance of the reference image so as to regain luminance before performing correction. Thereby, all of the noises Sn commonly included in the measurement image and the reference image are removed from the measurement image obtained after such correction (measurement image data $D32b$).

Measurement image data $D33b$ obtained after correction for removing noises $Sn$=$(D31a/D32a)$×(average value of $D32a$)  (20)

Thus, in the modification, in the case where the transmission contrast and the reflection contrast is determined by calculation, correction for removing the noises Sn is performed on the luminance distribution of the obtained picked-up image, and then the contrast is determined. Therefore, noises (such as flaws or dust) of the optical system, light intensity unevenness of the light source or the like may be removed, and the crystallinity evaluation precision may be further improved.

FIG. 24 illustrates an example of the transmission image before performing correction for removing such noises Sn, and FIG. 25 illustrates an example of the transmission image obtained after such correction. In a practical example, the gate electrode 21, the gate insulating films 221 and 222, the a-Si film 230, a buffer layer and the light-absorbing layer 231 were formed in this order on the transparent substrate 20, and then an annealing process was performed through the use of the laser light L1 by the laser diode to form microcrystalline silicon on the transparent substrate 20. Then, as described above, after the measurement image, the reference image and the zero level image were obtained through the use of the irradiation light Lout from the LED 12, and then the evaluation of the transmission contrast was performed before and after performing correction for removing the noises Sn. Moreover, the same measurement at the same measurement point was repeated a plurality of times to evaluate variations in measurement data (refer to FIG. 26). It was obvious from FIGS. 24 to 26 that the noises Sn existing in a circle in FIG. 24 or the like were removed by correction, thereby variations in contrast measurement data after the correction was reduced by approximately 48% of variations before the correction.

Although the present invention is described referring to the embodiment and the modifications, the invention is not limited thereto, and may be variously modified.

For example, in the above-described embodiment or the like, the case where when the transmission image of the p-Si film 23 (the transmission image data D1) is obtained, green light is used as light (irradiation light Lout) applied to the p-Si film 23 and the a-Si film 230 is described. However, the wavelength region of the irradiation light Lout is not limited to the wavelength region of green light. More specifically, for example, in the case where white light is used, measurement may be performed with high sensitivity without a process of removing the light-absorbing layer 231. Moreover, in the case where light with a shorter wavelength than that of blue light, sensitivity after removing the light-absorbing layer 231 may be improved. Further, light with a shorter wavelength than that of blue light is effective in measurement of reflected light on a pattern. In addition, an image pickup means for obtaining the transmission image is not limited to the objective lens 13 and the CCD camera 14 described in the above-described embodiment or the like, and may be configured of any other optical system.

Moreover, in the above-described embodiment or the like, the case where laser light L1 is applied through the use of a laser diode light source when forming the p-Si film 23 (in the annealing process) is described. However, a laser light source of any other kind, for example, a gas laser such as an excimer laser may be used.

Further, in the above-described embodiment or the like, the case where a transmission image from the back side of the substrate is used. However, a transmission image from a front side of the substrate may be used. In this case, the substrate is not necessarily a transparent substrate, and the movable stage 11 does not necessarily allow the irradiation light Lout to pass therethrough.

In the above-described embodiment or the like, the case where the picked-up image of the p-Si film 23 and the a-Si film 230 (the transmission image or the reflection image) is obtained on the basis of the transmitted light or the reflected light of the irradiation light Lout, and the contrast (the transmission contrast or the reflection contrast) is determined on the basis of the picked-up image is described. However, for example, the contrast (the transmission contrast or the reflection contrast) may be determined by performing spectrophotometric measurement on the basis of light Lout applied to a microscopic region instead of such a picked-up image. In the case where evaluation is performed by such spectrophotometric measurement, compared to the case where the picked-up image is used, the precision of the evaluation is lower, but the evaluation may be performed at higher speed.

Figures 26, 27:
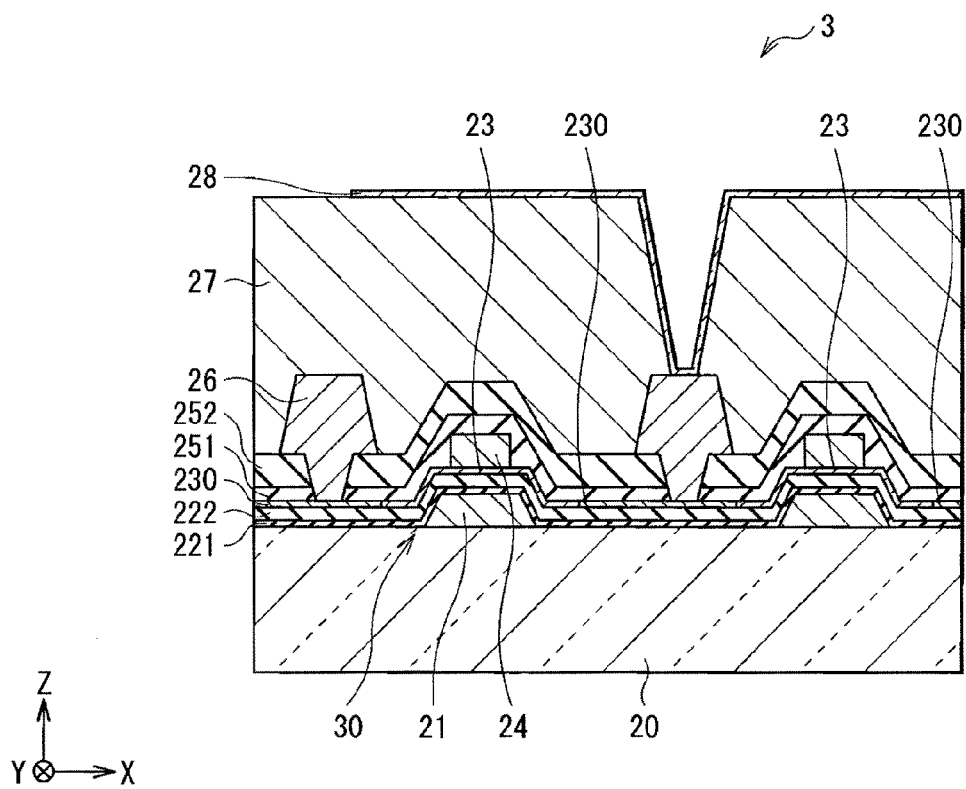
FIG. 26 is an illustration of an example of variations in contrast before and after the correction process according to the modification 9.
FIG. 27 is a sectional view illustrating an example of the configuration of a TFT substrate including the semiconductor thin film formed by the steps of FIGS. 2 to 5.

For example, as illustrated in FIG. 27, the p-Si film 23 described in the above-described embodiment or the like is applicable to a TFT substrate 3 including a bottom gate thin film transistor (TFT) used for manufacturing a liquid crystal display or an organic EL display. More specifically, in the Si thin film substrate 2 obtained after performing the inspection process described in the above-described embodiment or the like, interlayer insulating films 251 and 252, a wiring 26, a planarization film 27 and a transparent conductive film 28 may be formed in this order on the p-Si film 23 by, for example, a photolithography method. At this time, the interlayer insulating film 251 is made of, for example, silicon nitride ($SiN_X$), the interlayer insulating film 252 is made of, for example, silicon oxide ($SiO_2$), the wiring 26 is made of, for example, aluminum (Al), the planarization film 27 is made of, for example, an acrylic resin or the like, and the transparent conductive film 28 is made of, for example, ITO (Indium Tin Oxide). Although the TFT substrate including a bottom gate TFT is illustrated in FIG. 20, for example, a semiconductor thin film formed in the invention is applicable to a TFT substrate including a top gate TFT. Moreover, the semiconductor thin film formed in the invention is not limited to a semiconductor thin film used for the formation of such a TFT, and may be applied to any other semiconductor device.

Further, in the above-described embodiment or the like, as examples of the amorphous semiconductor thin film and the crystalline semiconductor thin film, the Si thin films (the a-Si film 230, the p-Si film 23 and the microcrystalline Si film) are described. However, the invention is applicable to any other semiconductor thin film (for example, all semiconductor thin films in which a difference between the gray levels of an irradiated region and a non-irradiated region is measurable such as a SiGe thin film) in addition to the Si thin film.

The present application contains subject matter related to that disclosed in Japanese Priority Patent Application JP 2008-135806 filed in the Japanese Patent Office on May 23, 2008, and Japanese Priority Patent Application JP 2009-020686 filed in the Japanese Patent Office on Jan. 30, 2009, the entire contents of which are hereby incorporated by references.

It should be understood by those skilled in the art that various modifications, combinations, sub-combinations and alterations may occur depending on design requirements and other factors insofar as they are within the scope of the appended claims or the equivalents thereof.

What is claimed is:

1. A method of forming a semiconductor thin film comprising the steps of:

forming an amorphous semiconductor thin film on a substrate;

forming a crystalline semiconductor thin film partially in each element region by applying laser light to the amorphous semiconductor thin film to selectively perform a heating process on the amorphous semiconductor thin film, thereby crystallizing the amorphous semiconductor thin film in a region irradiated with the laser light; and inspecting the crystallinity degree of the crystalline semiconductor thin film, wherein the step of inspecting includes the steps of determining a contrast between the luminance of a crystallized region and the luminance of a non-crystallized region by applying light to the crystalline semiconductor thin film and the amorphous semiconductor thin film, and performing screening of the crystalline semiconductor thin film on the basis of the determined contrast.

2. The method of forming a semiconductor thin film according to claim 1, wherein in the step of performing screening, screening of the crystalline semiconductor thin film is performed through the use of a correlation between the determined contrast, irradiation intensity of light in the step of determining the contrast, and electrical characteristics obtained in the crystalline semiconductor thin film.

3. The method of forming a semiconductor thin film according to claim 2, wherein screening of the crystalline semiconductor thin film is performed through the use of γ characteristics with a γ value=1 between the irradiation intensity and the contrast.

4. The method of forming a semiconductor thin film according to claim 2, wherein γ characteristics between the irradiation intensity and the contrast are corrected so as to have a γ value=1, and then screening of the crystalline semiconductor thin film is performed through the use of the corrected γ characteristics.

5. The method of forming a semiconductor thin film according to claim 1, wherein in the step of determining the contrast, a picked-up image of the crystalline semiconductor thin film and the amorphous semiconductor thin film is obtained on the basis of applied light, and then the contrast is determined on the basis of the picked-up image.

6. The method of forming a semiconductor thin film according to claim 5, wherein a transmission image of the crystalline semiconductor thin film and the amorphous semiconductor thin film is obtained on the basis of transmitted light of the applied light, and then the contrast is determined on the basis of the transmission image.

7. The method of forming a semiconductor thin film according to claim 5, wherein a reflection image of the crystalline semiconductor thin film and the amorphous semiconductor thin film is obtained on the basis of reflected light of the applied light, and then the contrast is determined on the basis of the reflection image.

8. The method of forming a semiconductor thin film according to claim 5, wherein a reference level measurement region for obtaining a reference image with respect to the picked-up image and a zero level measurement region for obtaining a zero level image corresponding to an offset component when obtaining the picked-up image and the reference image are arranged in predetermined positions on the substrate or a stage where the substrate is mounted, and in the step of determining the contrast, correction is performed on a luminance distribution of the obtained picked-up image through the use of the following expression, and then the contrast is determined;

(luminance distribution of picked-up image after correction)={(luminance distribution of picked-up image before correction−luminance distribution of zero level image)/(luminance distribution of reference image−luminance distribution of zero level image)}×{average value of (luminance distribution of reference image−luminance distribution of zero level image)}.

9. The method of forming a semiconductor thin film according to claim 1, wherein in the step of determining the contrast, spectrophotometric measurement is performed on the basis of light applied to a microscopic region to determine the contrast.

10. The method of forming a semiconductor thin film according to claim 1, wherein in the step of determining the contrast, applied light is divided into a plurality of beams, and the luminance of the crystallized region and the luminance of the non-crystallized region are differentially amplified, and then the contrast is determined.

11. The method of forming a semiconductor thin film according to claim 1, wherein in the step of determining the contrast, white light is used as applied light.

12. The method of forming a semiconductor thin film according to claim 1, wherein in the step of determining the contrast, green light is used as applied light.

13. The method of forming a semiconductor thin film according to claim 1, wherein in the step of determining the contrast, light with a shorter wavelength than that of blue light is used as applied light.

14. The method of forming a semiconductor thin film according to claim 1, wherein in the step of forming the crystalline semiconductor thin film, the laser light is applied to a light-absorbing layer, thereby a heating process is performed indirectly on the amorphous semiconductor thin film.

15. The method of forming a semiconductor thin film according to claim 1, wherein in the step of forming the crystalline semiconductor thin film, the laser light is applied through the use of a laser diode light source.

16. The method of forming a semiconductor thin film according to claim 1, wherein the crystalline semiconductor thin film is a film used to form a TFT (a thin film transistor).

17. The method of forming a semiconductor thin film according to claim 1, wherein the crystalline semiconductor thin film and the amorphous semiconductor thin film are Si (silicon) thin films.

18. The method of forming a semiconductor thin film according to claim 17, wherein the crystalline semiconductor thin film is a polycrystalline Si thin film or a microcrystalline Si thin film.

19. A semiconductor thin film inspection apparatus being a crystallinity degree inspection apparatus used to form a crystalline semiconductor thin film, the crystalline semiconductor thin film being formed partially in each element region by applying laser light to an amorphous semiconductor thin film on a substrate to selectively perform a heating process on the amorphous semiconductor thin film, thereby crystallizing the amorphous semiconductor thin film in a region irradiated with the laser light, the semiconductor thin film inspection apparatus comprising:

a stage on which the substrate is mounted, the substrate including the crystalline semiconductor thin film formed thereon;

a light source applying light to the crystalline semiconductor thin film and the amorphous semiconductor thin film;

a derivation section determining a contrast between the luminance of a crystallized region and the luminance of a non-crystallized region on the basis of light emitted from the light source; and a screening section performing screening of the crystalline semiconductor thin film on the basis of the contrast determined by the derivation section.

20. The semiconductor thin film inspection apparatus according to claim 19, further comprising: a control section performing control for relatively displacing the light source and an optical system of the derivation section with respect to the substrate mounted on the stage.

* * * * *